US006355864B1

(12) United States Patent
Shi et al.

(10) Patent No.: US 6,355,864 B1
(45) Date of Patent: Mar. 12, 2002

(54) VERSATILE RPL34 PROMOTER ELEMENTS AND USE THEREOF

(75) Inventors: Lifang Shi; Ziyu Dai; Johnway Gao, all of Richland; Brian S. Hooker, Kennewick; Daniel B. Anderson, Pasco, all of WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 09/417,019

(22) Filed: Oct. 12, 1999

Related U.S. Application Data

(63) Continuation-in-part of application No. 09/358,394, filed on Jul. 22, 1999, now abandoned.
(51) Int. Cl.⁷ .................... C07H 21/04; C12N 15/00; C12N 15/63; C12N 5/14; A01H 5/00
(52) U.S. Cl. ................. 800/298; 435/69.1; 435/320.1; 435/419; 536/24.1
(58) Field of Search ............................ 435/320.1, 410, 435/468, 69.1, 419; 536/24.1; 800/298

(56) References Cited

U.S. PATENT DOCUMENTS 5,097,025 A    3/1992   Benfey et al.

OTHER PUBLICATIONS

Ziyu Dai et al, Promoter elements controlling developmental and environmental regulation of a tobacco ribosomal protein gene L34, Plant Molecular Biology 32: 1055–1065, 1996.*
Breathnach et al.: "Organization and Expression of Eucaryotic Split Genes Coding for Proteins", Annual Review of Biochemistry, vol. 50, 1981.
Khoury et al.: Enhancer Elements, Cell, vol. 33, Jun. 1983, pp 313–314.
Benoist et al.: "In vivo sequence requirements of the SV40 early promoter region", Nature, vol. 290, No. 5804, Mar. 26, 1981, pp 304–310.
Gruss et al.: "Simian virus 40 tandem repeated sequences as an element of the early promoter", Proceedings of the National Academy of Sciences of the United States of America, vol. 78, No. 2, Feb. 1981, pp 943–947.
Ellis et al.: "The ocs element: a 16 base pair palindrome essential for activity of the octopine synthase enhancer", The EMBO Journal, vol. 6, No. 1, Nov. 1987, pp 3203–3208.
Singh et al.: Saturation mutagenesis of the octopine synthase enhancer: Correlation of mutant pheneotypes with binding of a nuclear protein factor,Proceedings of the National Academy of Sciences of the United States of America, vol. 86, No. 10, May 1989, pp 3733–3737.
Comai et al.: "Novel and useful properties of a chimeric plant promoter combining CaMV 35S and MAS elements", Plant Molecular Biology, vol. 15, No. 3, Sep. 1990, pp 373–381.

Gao et al.: "Developmental and environmental regulation of two ribosomal protein genes in tobacco", Plant Molecular Biology, vol. 25, No. 5, Aug. 1994, pp761–770.
Dai et al.: "Promoter elements controlling developmental and environmental regulation of a tobacco ribosomal protein gene L34", Plant Molecular Biology, vol. 32, No. 6, Dec. (ii) 1996, pp 1055–1065.
Dai et al.: 1994, Supra.
Brisson et al.: "Expression of a bacterial gene in plants by using a viral vector", Nature, vol. 310, No. 5977, Aug. 9–15, 1984, pp 511–514.
Odell et al.: "Identification of DNA sequences required for activity of the cauliflower mosaic virus 35S promoter", Nature, vol. 313, No. 6005, Feb. 28–Mar. 6, 1985, pp 810–812.
Gowda et al.: "Plant Gene Transfer", UCLA Symposia on Molecular & Cellular Biology, Journal of Cellular Biochemistry, Supplement 13D, 1989.
Takamatsu et al.: Expression of bacterial chloramphenicol acetyltransferase gene in tobacco plants mediated by TMV–RNA, The EMBO Journal, vol. 6, No. 2, Feb. 1987, pp307–311.
Coruzzi et al.: "Tissue–specific and light–reulated expression of a pea nuclear gene encoding the small subunit of ribulose–1,5–bisphosphate carboxylase", The EMBO Journal, vol. 3, No. 8, Aug. 1984, pp–1671–1679.
Broglie et al.: "Light–Regulated Expression of a Pea Ribulose–1,5–Bisphosphate Carboxylase Small Subunit Gene in Transformed Plant Cells", Science, vol. 224, No. 4651, May 25, 1984, pp 838–843.
Velten et al.: "Islolation of a dual plant promoter fragment from the Ti plasmid of Agrobacterium tumefaciens", The EMBO Journal, vol. 3, No. 12, Dec. 1, 1984, pp 2723–2730.
Gurley et al.: "Upstream Sequences Required for Efficient Expression f a Soybean Heat Shock Gene", Molecular and Cellular Biology, vol. 6, No. 2, Feb. 1986, pp 559–565.
Severin et al.: "Heat–inducible hygromycin resistance in transgenic tobacco", Plant Molecular Biology, vol. 15, No. 6, Dec. 1990, pp 827–833.
Mett et al.: "Copper–controllable gene expression system for whole plants", Proceedings of the National Academy of Sciences of the United States of America, vol. 90, No. 10, May 15, 1993, pp4567–4571.
Hershey et al.: "Isolation and characterization of cDNA clones for RNA species induced by substituted benzenesulfonamides in corn", Plant Molecular Biology, vol. 17, No. 4, Oct. 1991, pp 679–690.

(List continued on next page.)

Primary Examiner—David Guzo
Assistant Examiner—Lauren Nguyen
(74) Attorney, Agent, or Firm—Foley & Lardner

(57) ABSTRACT

Synergistically functional, yet separable, cis-acting enhancer elements from the rpL34 promoter are disclosed. These enhancer elements of the instant invention may be used in combination with a plurality of promoters to increase gene expression without affecting the intrinsic specificity of the promoters. Also disclosed are methods for using the enhancer elements of the instant invention as well as vectors and transgenic plants comprising the enhancer elements.

16 Claims, 14 Drawing Sheets

OTHER PUBLICATIONS

Schena et al.: "A steroid–inducible gene expression system for plant cells", Proceedings of the National Academy of Sciences of the United States of America, vol. 88, No. 23, Dec. 1, 1991, pp 10421–10425.

Ito et al.: Meristem–specific gene expression directed by the promoter of the S–phase–specific gene, cyc07, in transgenic Arabidopsis, Plant Molecular Biology, vol. 24, No. 6, Mar. (ii) 1994, pp863–878.

Martinez et al.: "Spatial patern of cdc2 expression in relation to meristem activity and cell proliferation during plant development", Proceedings of the National Academy of Sciences of the United States of America, vol. 89, No. 16, Aug. 15, 1992, pp 7360–7364.

Medford et al.: "Molecular Cloning and Characterization of Genes Expressed in Shoot Apical Meristems", The Plant Cell, vol. 3, No. 4, Apr. 1991.

Terada et al.: "A wheat histone H3 promoter confers cell division–dependent and –independent expression of the gus A gene in trangenic rice plants", The Plant Journal, vol. 3, No. 2, 1993, pp 241–252.

Wissenbach et al.: "Myb genes from Hordeum vulgare: tissue–specific expression of chimeric Myb promoter/Gus genes in transgenic tobacco", The Plant Journal, vol. 4, No. 3, 1993, pp 411–422.

Methods in Enzymology, vol. 153, 1987, Wu and Grossman, Eds., Academic Press.

"Gene Transfer in Plants: Production of Transformed Plants Using Ti Plasmid Vectors", Methods for Plant Molecular Biology, Weissbach & Weissbach, 1988, Academic Press, N.Y., Section VIII, pp 423–463.

Grierson et al.: "Genetic Transformation of Plants by Agrobacterium", Plant Molecular Biology, Chapter Seven, pp 141–211.

Horsch: "A Simple and General Method for Transferring Genes into Plants", Science, vol. 227, No. 4691, 1985, pp 1229–1231.

De Framond et al.: "Mini–Ti: A New Vector Strategy for Plant Genetic Engineering", Bio/Technology, May 1983, pp 262–269.

Hoekama et al.: "A binary plant vector strategy based on separation of vir–and T–region of the Agrobacterium tumefaciens Ti–plasmid", Nature, vol. 303,, No. 5913, May 12–18, 1983, pp179–180.

Bechtold et al.: "In planta Agrobacterium mediated genetransfer by infiltration of adult *Arabidopsis thaliana* plants", Life Sciences, vol. 316, No. 10, Oct. 1993, pp 1194–1199.

Fromm et al.: "Expression of genes transferred into monocot and dicot plant cells by electroporation", Proceedings of the National Academy of Sciences of the United States of America, vol. 82, No. 17, Sep. 1985, pp 5824–5828.

Klein et al: "High–velocity microprojectiles for deliving nucleic acids into living cells", Nature, vol. 327, No. 6117, May 7–13, 1987, pp 70–73.

Ebert et al.: "Identification of an essential upstream element in the nopaline synthase promoter by stable and transient assays", Proceedings of the National Academy of Sciences of the United States of America, vol., 84, No. 16, Aug. 1987, pp 5745–5749.

An et al.: "Binary vectors", Plant Molecular Biology Manual, pp PMAN–A3/1–PMAN–A3/19.

An: "Binary Ti Vectors for Plant Transformation and Promoter Analysis", Methods in Enzymology, vol. 153, Part D,, pp 293–305.

Murashige et al.: "A Revised Medium for Rapid Growth and Bio Assays with Tobacco Tissue Cultures", Physiologia Plantarum, vol. 15 Fasc. 2, 1962, pp 473–497.

Jefferson et al.: "GUS fusions: β–glucuronidase as a sensitive and versatile gene fusion marker in higher plants", The EMBO Journal, vol. 6, No. 13, Dec. 20, 1987, pp 3901–3907.

White et al.: "Directed mutagenesis and mutant analysis", Gene Probes 2 A Practical Approach, pp 329–355.

McKnight et al.: "Transcriptional Control Signals of a Eukaryotic Protein–Coding Gene", Science, vol. 217, No. 4557, Jul. 13, 1982, pp 316–324.

* cited by examiner

```
------CGGCCTGCAGCA-----------------------------
-----------GGCCTGCAGCA--------------------------      LS1 (194-181)-GUS-nos
-----------------CGGCCTGCAGCA-------------------      LS2 (181-171)--------
-----------------------------CGGCCTGCAGCA------      LS3 (170-159)--------
-----------CGGCCTGCAGGATCGTCGACCAC--------------      LS4 (158-147)--------
------------CGGCCTGCAGGATCGTCGACCACTGTTGATGGGCTTATAGCCCGTCTGATTT      LS5 (181-159)--------
TTGTTTAAACCCAGTTTAATGGGCTAACATGTTGATGGGCTTATAGCCCGTCTGATTT           -1500
```

Fig. 6a

1. Δ 46-35S
2. Δ 800-35S
3. 5A-35S
4. 4C-35S
5. 2 (A+B+C) -35S
6. 3B-35S
7. 3 (A+B) -35S
8. -1500
9. Δ 128
10. Mac

```
-438                        AGATCTCT CTTTGTATTC TTATTGATGT ACTGGTTTGA

-400 AGATGAATAA AATCTTTCAT TCCACCAAAA AAAGAATGAA AATAAAATTT

-350 TAATATACAT GTTGATATAG ACAAAGAAGA AAAAAAAAGT TGTGATTACA

-300 TTTATTGACT ATTTGATGCC AATATCTATA ACTAGAGCTA TTTTCTATCA

-250 ATTATATGGG TATGTTGTTA TACCATGCCA AAACCTCAAT TCATAATGTG

-200 CTTGTTTAAA CCCAGTTTAA TGGGCTAACA TGTTGATGGG CTTATAGGCC
                                   -179
-150 CGTCTGATTT CCTTGCCAGA CACTAGTAAG TAAATGATTC TATCATCCAA
                                   -129
-100 TATCAACCGT GGGATCTAGG GCTTGTCCCA CTTATATACA CTACATATAT

-50  TTAACTTTCC TTTAGCCCTT CTGCTTCAGC CCCCAAAACA AAGAAAGAAG

+1   CTACAGAGAG AATAGCAGCG CCGCCGTGAA AAATG
```

Fig. 10

VERSATILE RPL34 PROMOTER ELEMENTS AND USE THEREOF

This application is a continuation-in-part application of U.S. Ser. No. 09/358,394, filed Jul. 22, 1999, now abandoned.

BACKGROUND OF THE INVENTION

1. Field of the Invention

The present invention relates generally to gene expression in transgenic plants. More specifically, the present invention relates to unique enhancer elements from the tobacco rpL34 promoter which when operably linked to a promoter, increase the promoter's rate of transcription and/or alter its activity in transformed plant cells.

2. Description of the Related Art

Given the technological advances in recombinant DNA technology made over the past decade it has become common practice to introduce new genetic material into plant cells, plant tissues or a whole plant to establish new traits that enhance the value of the plant or plant tissues. Both angiosperm and gymnosperm higher plants are included within the definition of "plant."

A typical eukaroytic gene consists of a promoter region, introns, exons and a transcription terminator. The promoter region is typically located upstream of the transcribed region. The promoter determines the level and specificity of the gene transcription.

In eukaryotic organisms such as a plant, a promoter is not recognized directly by a RNA polymerase. Transcription initiation factors (TIFs) first bind to a promoter to form a preinitiation complex, and only then does an RNA polymerase bind to form an initiation complex.

A promoter for RNA polymerase II consists of a transcription initiation region, generally including a TATA box (the "Goldberg-Hogness Box") and frequently a CCAAT box, as well as upstream cis-acting elements. The transcription initiation region is also called the minimal promoter because it is the minimal DNA sequence required for a gene transcription. The TATA box directly binds a transcription factor complex that includes RNA polymerase II, for the initiation of DNA transcription. The TATA box is located approximately 25 base pairs upstream of the transcription start site. Further upstream, often between nucleotides −80 and −100, there can be a promoter element with homology to the consensus sequence CCAAT. Breathnach et al., *Ann. Rev. Biochem.* 50:349–383 (1981). In plants, the CCAAT box may be substituted by the AGGA box, at a similar distance from the transcription start site. Messing et al., in *Genetic Engineering of Plants,* Kosuge et al. Eds., pages. 211–227.

Promoters, together with enhancers and silencers, are cis-acting elements that control gene expression. Promoters are positioned next to the transcription start site and function in an orientation-dependent manner. Enhancer and silencer elements, which modulate the activity of promoters, may effect promoter activity in either orientation and at greater distances from the transcription start site. Khoury et al., *Cell* 33:3–13 (1983).

Enhancers can greatly increase the rate of transcription, and can generally function in either orientation and at various distances upstream or downstream from a given promoter. Enhancers may function in a wide variety of cells, or they may show strict cell or organism specificity. Enhancers may affect gene expression in response to environmental stimuli, such as illumination, nutrient concentration, heat shock, wounding, and anaerobiosis. These elements may also control gene expression in a development-specific, tissue-specific or tissue-preferred manner.

The prototype enhancer, the 72 bp tandem repeat of SV40 DNA, was initially identified as a cis-acting element located more than 100 base pairs upstream from the transcription initiation site of the early viral genes (Benoist et al., *Nature* 290:304–310 (1981); Gruss et al., *Proc. Natl. Acad. Sci. USA* 78:943–947 (1981). Deletion of this element reduced early gene expression by a factor of at least 100. Known cis-acting elements that enhance transcription in plants include a 16-bp palindrome sequence (5'-ACGTAAGCGCTTACGT-3') (SEQ ID NO: 4) derived from the octopine synthase gene (Ellis et al., *EMBO J* 6:3203 (1987) and the B-domain of the Cauliflower Mosaic Virus (CaMV) 35S promoter (Benfey et al. U.S. Pat. No. 5,097,025 (1992). A single and double base substitution or deletion in the ocs element caused significant loss in enhancer activity (Singh et al., *Proc. Natl. Acad. Sci. USA* 86:3733–3737 (1989). The mac gene promoter, which is composed of the mannopine synthase (mas) promoter from the *Agrobacterium tumefaciens* octopine Ti plasmid, and the B-domain of the 35S promoter, has much higher activity than that of the native 35S promoter, 35S promoter plus B-domain of the 35S promoter, or the mas promoter (Comai et al., *Plant Mol. Biol.* 15:373–381 (1990).

Synthesis of ribosomal proteins is universal in plant growth and development and represents an excellent model system for studying plant gene expression. Ribosomes are composed of a large (L) and a small (S) subunit built of RNA (r-RNAs) and proteins (rp) components.

Similar to other organisms, the tobacco genome contains various large subunit ribosomal protein (rpL) genes. One of these genes, referred to as rpL34, has been cloned and analyzed in some detail. Gao et al., *Plant Mol Biol* 25:761–770 (1994), Dai et al., *Plant Mol. Biol.* 32:1055–1065 (1996). The expression of the rpL34 gene is induced by plant wounding and chemicals and is meristem-specific.

Typically, higher levels of expression of mRNA is desired to increase the level of expression of the protein encoded by this mRNA. In addition, development-specific expression patterns enable protein production in plants during desired developmental stages, for example, post-harvest synthesis of foreign proteins. Also, tissue-specific patterns of expression enable novel schemes for utilization of non-crop plant portions for protein production as well as conferring necessary traits, such as disease resistance or chemical tolerance, to specific tissues. As recombinant DNA techniques are increasingly being applied to higher plants, there is an increased need for novel promoter elements to enable artificial regulation of gene expression. Specifically, there is a need for novel promoter elements that enable high levels of expression that is temporally, environmentally or developmentally controllable.

SUMMARY OF THE INVENTION

It is therefore an object of the present invention to provide novel promoter elements that enable high level gene expression. It is another object of the present invention to provide novel, non-specific enhancer elements which increase the activity of a promoter without affecting the promoter's intrinsic specificity. The present invention also provides a method for increased gene expression at high levels in a temporally, environmentally or developmentally controlled manner.

In a first embodiment, the invention provides a promoter element consisting essentially of a polynucleotide molecule having the sequence of A which is −147 to −158 (SEQ ID NO:1) of FIG. 10, an enhancer element consisting essentially of a polynucleotide molecule having the sequence of B which is −159 to −181 (SEQ ID NO:2) of FIG. 10; an enhancer element consisting essentially of a polynucleotide molecule having the sequence of C which is −182 to −197 (SEQ ID NO:3) of FIG. 10.

In another embodiment, the invention provides a recombinant promoter construct having the general formula (I) or (II):

$$[(A)_l, (B)_m, (C)_n, P] \qquad (I)$$

or $$[(A)_l, (B)_m, (C)_n]_q, P \qquad (II)$$

wherein A, B, and C are defined as above; and P is a native or non-native minimal promoter; and wherein A, B, C and P are operatively linked to each other and may be in any order; and wherein l, m, n are independent of each other and may be any integer between 0–5, and q is any integer between 1–5, provided that l, m and n are not simultaneously zero; and provided that the native configuration of the rpL34 promoter is excluded.

A preferred embodiment of the invention provides that P is selected from the group consisting of a constitutive promoter, a tissue-specific promoter and an inducible promoter.

Further embodiments of the invention provide a recombinant expression vector comprising the promoter elements, a plant cell comprising the expression vector, a transgenic plant regenerated from the cell and a method for producing a protein of interest using the transgenic plant.

a. Schematic drawing of rpL34 promoter internal deletion mutants placed upstream of the GUS reporter gene and nos terminator. −1500 contains the full length of the rpL34 promoter. Δ128 contains a deletion of the region −1500 to −128. m178 contains one base substitution at position −178, resulting in the creation of a NheI restriction site. Δ181/147 contains a deletion of the region of −181 and −147. The remaining constructs contain an internal deletion of the region −128 to the position indicated in the Figure named. SpeI and BglII cut at −128 and −438, respectively.

b and c. Transient and stable transformation analysis of the internally deleted rpL34 promoter. The averaged GUS activity for −1500 was assigned as 100 (lane 2). The GUS activities of the remaining constructs are normalized to that value. The standard error bars in 2b are derived from, at least, three independent transient assays. The GUS activity of at least 15 independently transformed plants was averaged in 2c. Lane 1, 3, 4, 5, 6, 7, 8, 9, and 10 represent activities from construct m178, Δ147, Δ159, Δ175, Δ185, Δ196, Δ210, Δ438, and Δ128, respectively.

Figure 3:
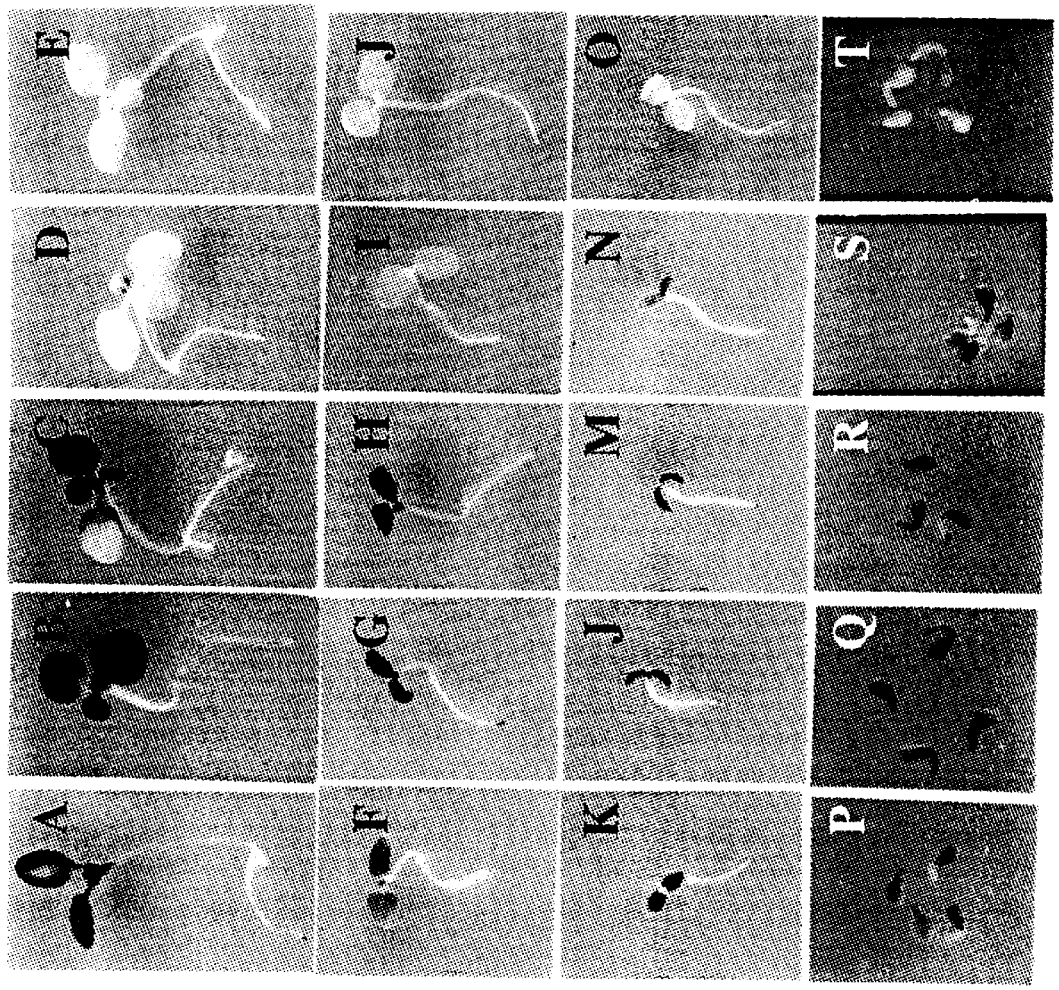

FIG. 3. Histochemical staining of transgenic tobacco. Panel A, F, K, and P are from m178; Panel B, G, J, and Q are from −1500; Panel C, H, M, and R are from Δ147; Panel D, I, N, and S are from Δ159; Panel E, J, O, and T are from Δ185. The plant materials are from germinating seeds, 4-, 6-, and 16-day-old seedlings.

Figure 4:
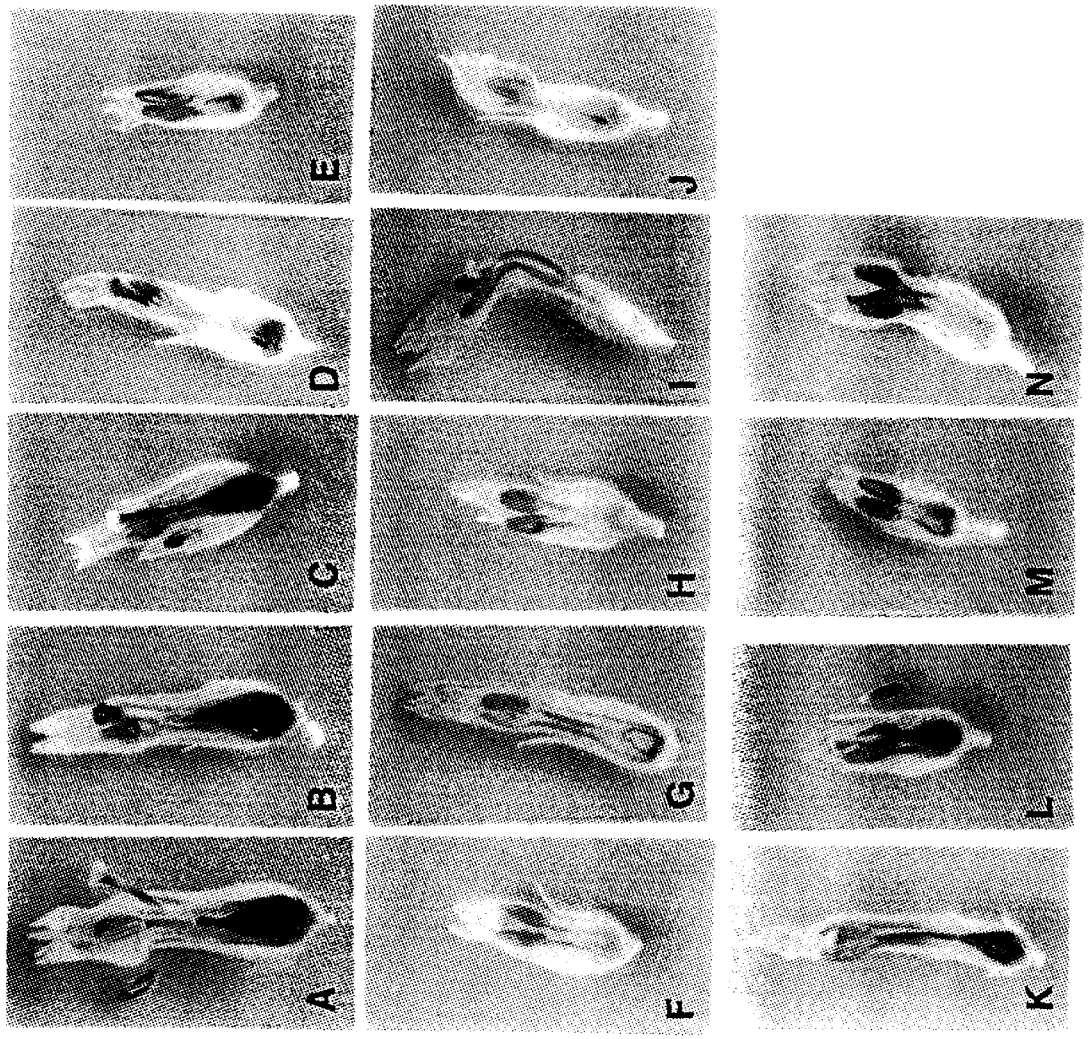

FIG. 4. Histochemical staining of transgenic tobacco flowers. Panel A to N represent m178, −1500, Δ147, Δ159, Δ175, Δ185, Δ196, Δ210, Δ438, Δ128, LS1, LS2, LS3, and Δ181/147, respectively.

Figure 5:
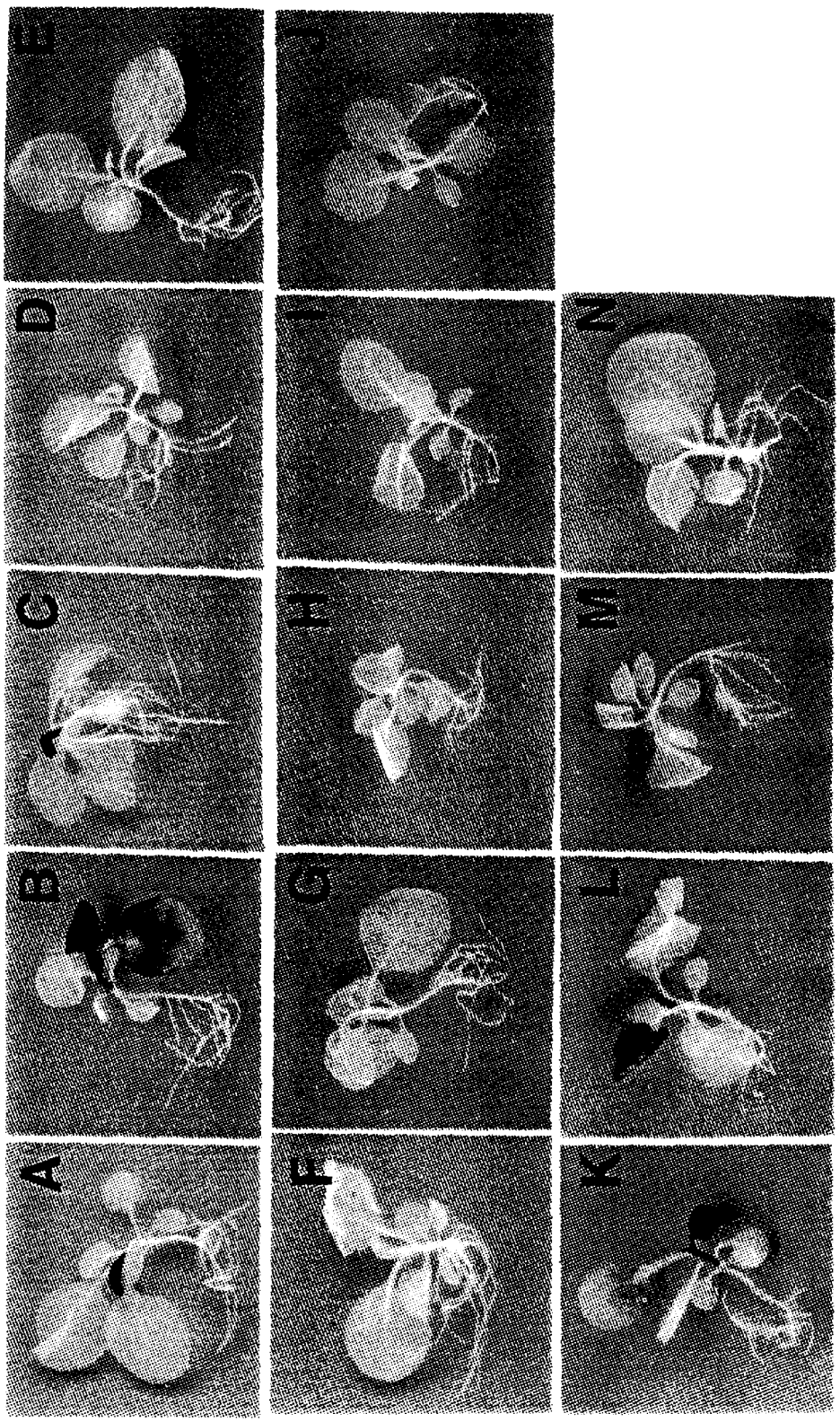

FIG. 5. Histochemical staining of 30-day-old tobacco plants. Panel A to N is from m178, −1500, Δ147, Δ159, Δ175, Δ185, Δ196, Δ210, Δ438, Δ128, LS1, LS2, LS3, and Δ181/147, respectively.

Figure 6B:
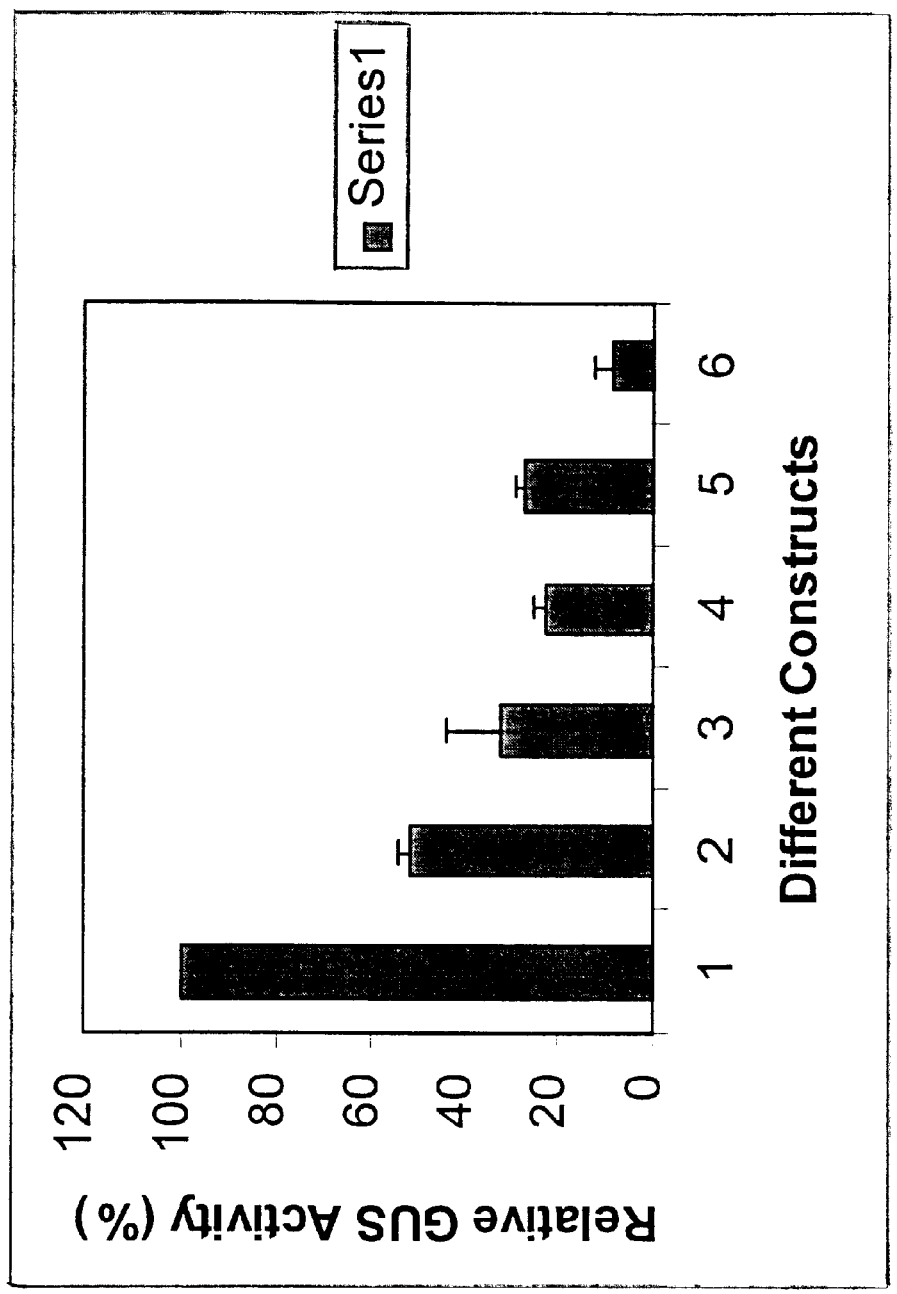
Figure 6C:
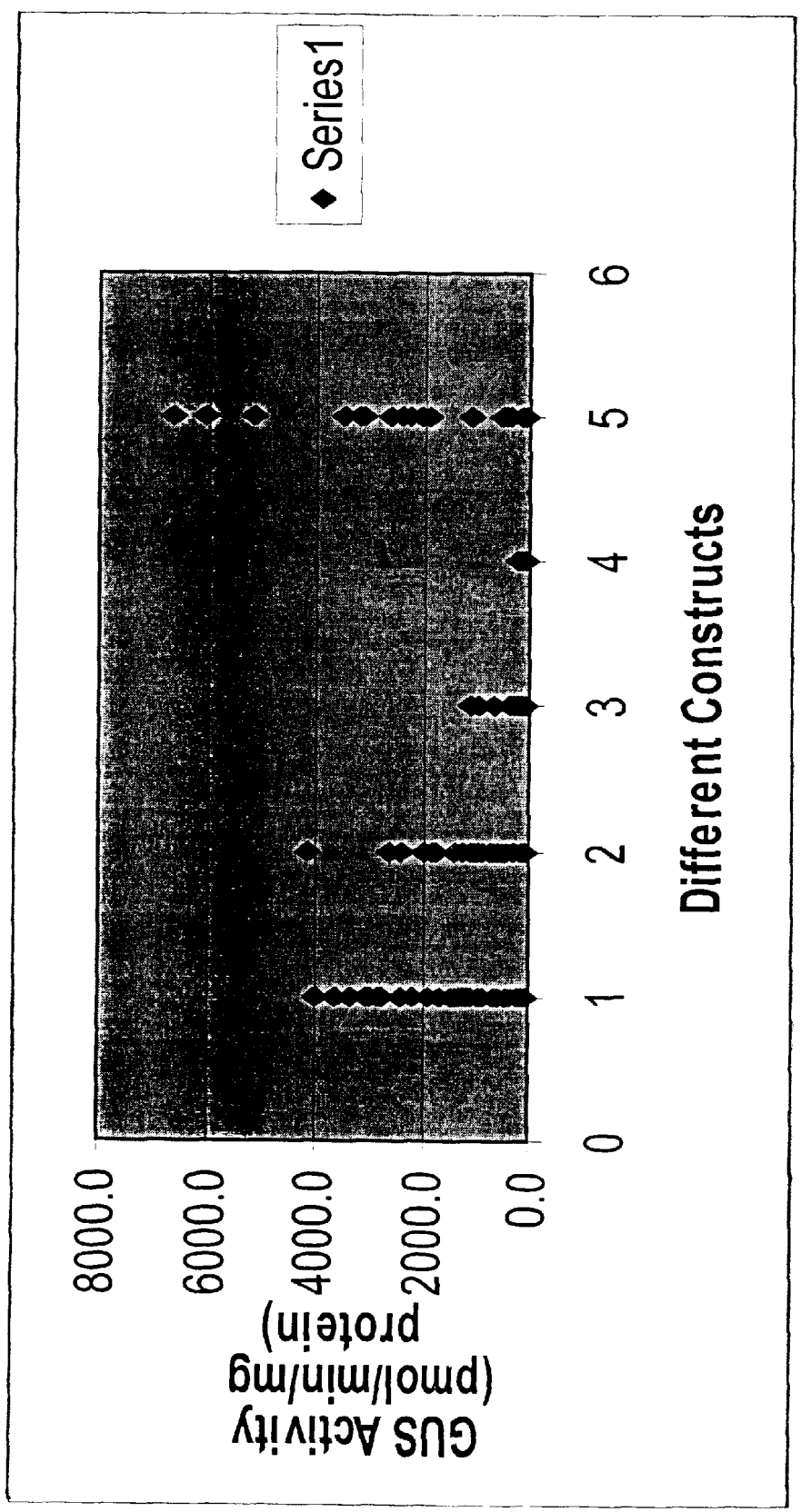

FIGS. 6a–c. Linker scanning mutation analysis of rpL34 promoter.

a. The linker scanning mutated sequence (SEQ ID NOS 23–26) in the rpL34 promoter region. The replaced regions are bolded with PstI sites underlined.

b. Transient analysis of linker scanning mutated rpL34 promoter constructs. Lanes 1 to 6 correspond to constructs −1500, LS1, LS2, LS3, LS4, and LS5. Reported GUS activities are normalized to the value for −1500, set at 100. The standard error bars in 6b are derived from, at least, three independent transient assays.

c. Stable transformation analysis of linker scanning mutated rpL34 promoter constructs. Each point represents the GUS activity of individual plants. Lanes 1 to 6 are from construct −1500, LS1, LS2, LS3, LS4, and LS5, respectively.

Figure 7A:
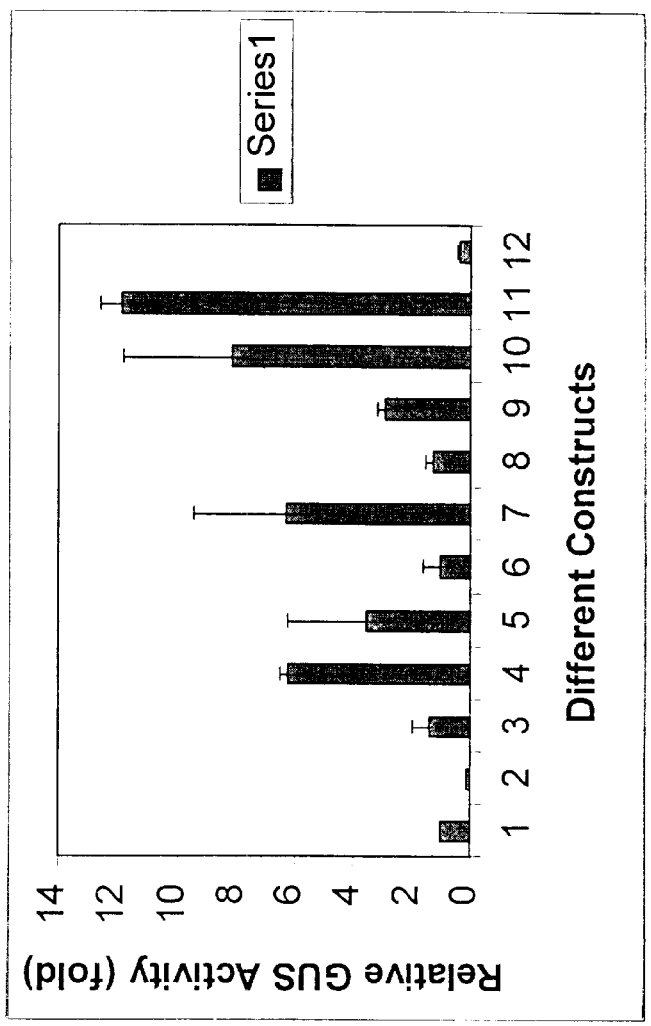
Figure 7B:
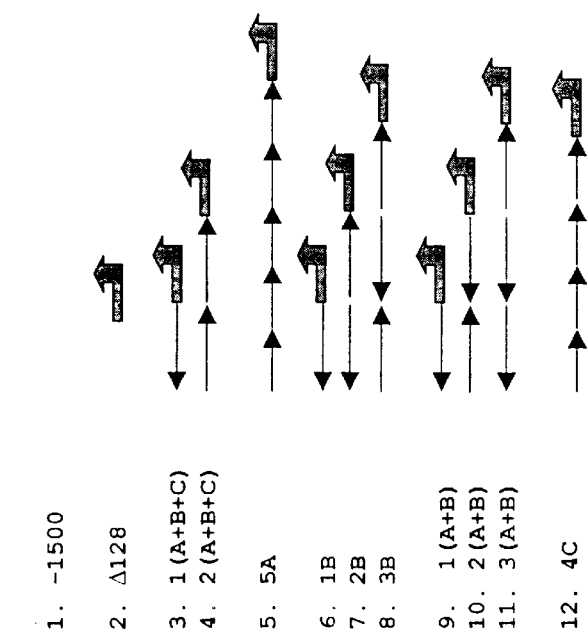

FIGS. 7a–b. Gain-of-function analysis of the rpL34 minimal promoter fused with rpL34 promoter fragments.

a. A, B, and C indicate DNA fragments in the region of −147 to −158, −159 to −181, and −182 to −197 in the rpL34 promoter, respectively. The small arrows indicate the orientation and copy number of the DNA fragment placed in front of Δ128. Both −1500 and Δ128 were described in FIG. 2a.

b. Relative GUS Activity (fold) of each construct in transient protoplast assays. The averaged GUS activity for −1500 was assigned as 1. The GUS activities of the remaining constructs are normalized to that value. Standard error bars are derived from three independent transient assays.

Figures 8A, 8B:
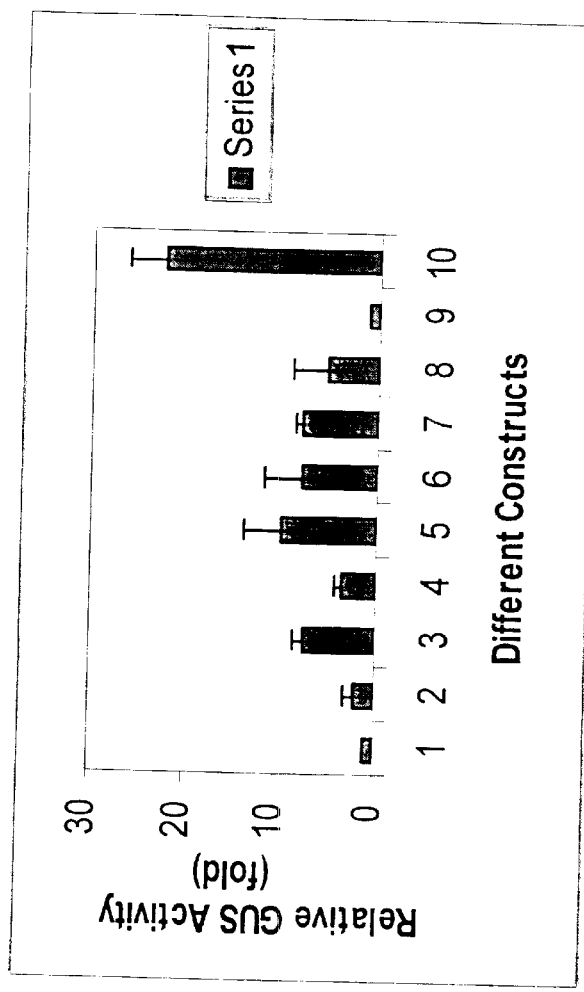

FIGS. 8a–b. Gain-of-function analysis of the 35S minimal promoter fused with rpL34 promoter fragments.

a. Construct Δ46-35S, indicated by the solid arrow, is the −46 35S minimal promoter fused with the GUS reporter gene and nos terminator. Construct Δ800-35S is the full length of the 35S promoter. A, B, and C indicate the DNA fragments in the region of −147 to −158, −159 to −181, and −182 to −197 of the rpL34 promoter, respectively. The term mac refers to the mac promoter, which is composed of the mannopine synthase (mas) promoter from the *Agrobacterium tumefaciens* octopine Ti plasmid and the B-domain of the 35S promoter, The small arrows indicate the orientation and copy number of the DNA fragment placed in front of Δ46-35S. Both −1500 and Δ128 were described in FIG. 2a.

b. Relative GUS Activity (fold) of each construct in transient protoplast assays. The averaged GUS activity for Δ46-35S was assigned as 1. The GUS activities of the remaining constructs are normalized to that value. Standard error bars are derived from three independent transient assays.

Figure 9:
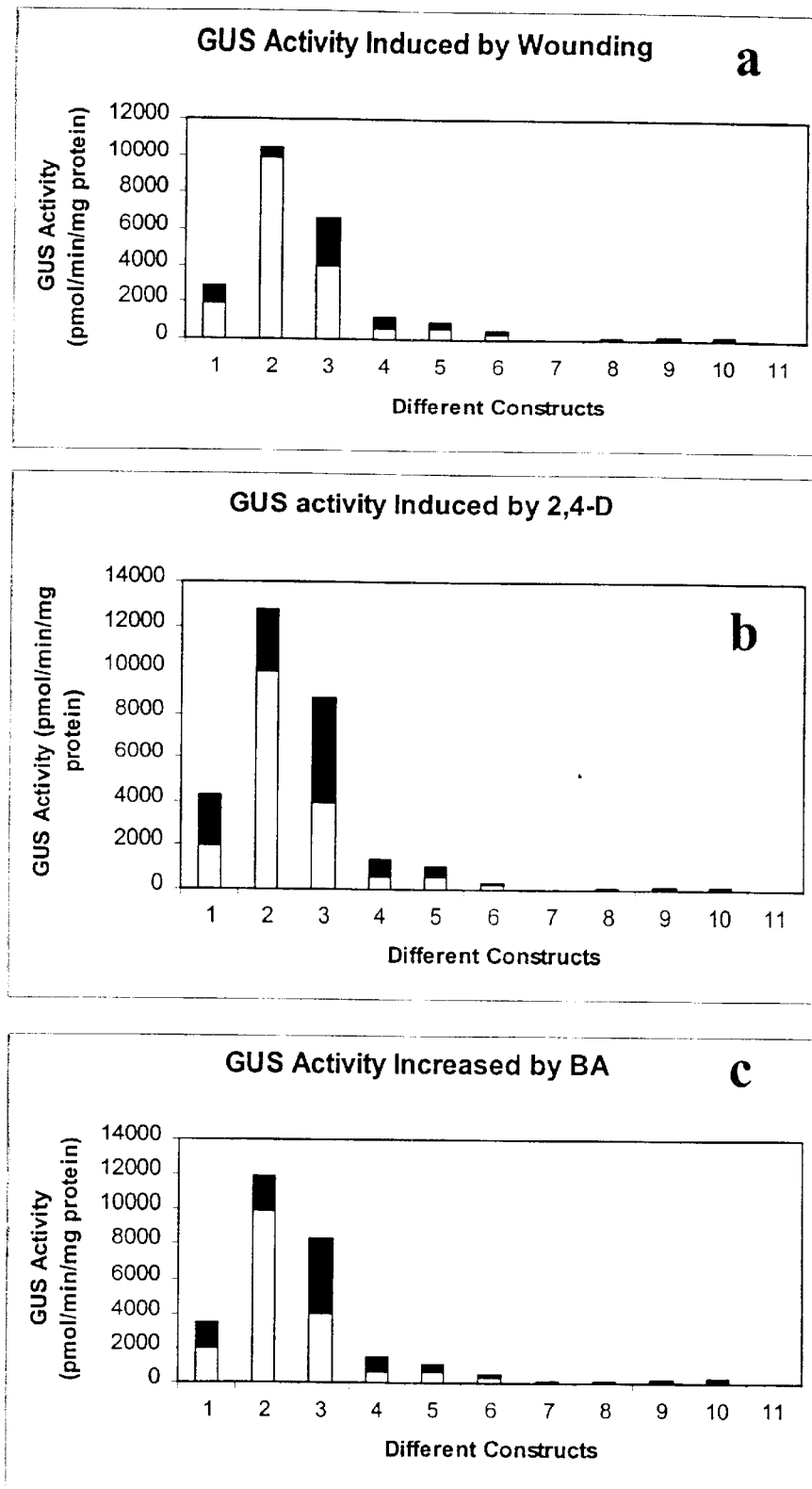

FIG. 9 The response of various deletion mutants of the rpL34 promoter to wounding and plant hormones. Leaf discs from the same transgenic tobacco plants were incubated with 1 μM 2,4-D (Panel b) or 5 μM BA (Panel c) in MS medium. Excised leaf discs incubated with no hormones were used for wounding experiments (Panel a) while the tissues ground immediately after excision were used as non-wounded controls. Lanes 1 to 11 are from transgenic tobacco containing construct m178, −1500, Δ147, Δ159, Δ175, Δ185, Δ196, Δ210, Δ438, Δ128, and Δ181/147, respectively. GUS activity for each plant before the treatment is presented in opened boxes, while the induced GUS activity is presented as filled boxes.

FIG. 10 The nucleotide sequence (SEQ ID NO: 28) of the 5'-upstream region of the rpL34 promoter from −438 to the translation initiation codon (+35). The CCAAT and TATA box regions are located from −104 to −97 and −57 to −50, respectively.

DETAILED DESCRIPTION OF THE PREFERRED EMBODIMENT

The present invention provides novel promoter elements, particularly enhancer elements, that enable high level gene expression of an operably linked gene. The enhancer elements according to the present invention may be combined with a plurality of other promoter elements to provide for enhanced gene expression and increased control of the gene expression via environmental and developmental parameters. The enhancer elements according to the present invention are particularly suitable for enhanced gene expression and regulation of transcription of plant genes.

The present invention also provides a novel, non-specific enhancer element which increases the activity of a promoter without affecting the promoter's intrinsic specificity.

The present invention further provides a method for increased gene expression at high levels in a temporally, environmentally or developmentally controlled manner.

1. Definitions

A structural gene is a DNA sequence that is transcribed into messenger RNA (mRNA) which is then translated into a sequence of amino acids characteristic of a specific polypeptide.

A promoter is a DNA sequence that directs the transcription of a gene, such as a structural gene, an antisense gene, a ribozyme gene or an external guide sequence gene. Typically, a promoter is located in the 5' region of a gene, proximal to the transcriptional start site. If a promoter is an inducible promoter, then the rate of transcription increases in response to an inducing agent. In contrast, the rate of transcription is not regulated or largely unregulated, by an inducing agent if the promoter is a constitutive promoter. A plant computable promoter is a promoter sequence that will direct the transcription of a gene in a plant cell.

A core promoter contains essential nucleotide sequences for promoter function, including the TATA box and start of transcription. By this definition, a core promoter may or may not have detectable activity in the absence of specific sequences that may enhance the activity or confer tissue specific activity. For example, the SGB6 core promoter consists of about 38 nucleotides 5'-ward of the transcriptional start site of the SGB6 gene, while the Cauliflower Mosaic Virus (CaMV) 35S core promoter consists of about 33 nucleotides 5'-ward of the transcriptional start site of the 35S genome.

A tissue-preferred promoter is a DNA sequence that, when operably linked to a gene, directs a higher level of transcription of that gene in a specific tissue than in some or all other tissues in an organism. For example, an anther-preferred promoter is a DNA sequence that directs a higher level of transcription of an associated gene in plant anther tissue.

An isolated DNA molecule is a fragment of DNA that has been separated from the DNA of an organism. For example, a cloned DNA molecule encoding an avidin gene is an isolated DNA molecule. Another example of an isolated DNA molecule is a chemically-synthesized DNA molecule, or enzymatically-produced cDNA, that is not integrated in the genomic DNA of an organism.

Complementary DNA (cDNA) is a single-stranded DNA molecule that is formed from a mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term expression refers to the biosynthesis of a gene product. For example, in the case of a structural gene, expression involves transcription of the structural gene into mRNA and the translation of mRNA into one or more polypeptides.

A cloning vector is a DNA molecule, such as a plasmid, cosmid, or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An expression vector is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked to" or "operatively linked to" the regulatory elements.

A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

A transgenic plant is a plant having one or more plant cells that contain a foreign gene.

In eukaryotes, RNA polymerase II catalyzes the transcription of a structural gene to produce mRNA. A DNA molecule can be designed to contain an RNA polymerase II template in which the RNA transcript has a sequence that is complementary to that of a specific mRNA. The RNA transcript is termed an antisense RNA and a DNA sequence that encodes the antisense RNA is termed an antisense gene. Antisense RNA molecules inhibit mRNA expression.

2. The rpL34 Promoter and Its Functional Elements

The enhancer elements of the present invention comprise the enhancer elements of the isolated rpL34 promoter. The rpL34 promoter has previously been identified, and a 50 bp upstream region has been shown to be essential for the promoter activity. See Dai et al., 1994, supra. However, it has been unclear which sequence elements within this upstream region play an important role in promoter activity.

The complete nucleotide sequence of the 5'-upstream region of the rpL34 promoter from −438 to the translation initiation codon (+35) is shown in FIG. 10 (SEQ ID NO:28).

An enhancer element is cis-acting and is generally upstream from and within 5000 bp of a promoter. However, an enhancer element may be downstream of a promoter. The enhancer element is preferably located within about 2000 bp, most preferably adjacent to, or within about 1000 bp of, the transcription initiation codon of the promoter. Conventionally, the initial nucleotide of the transcribed mRNA is designated +1, thus the sequence containing the enhancer is preferably located upstream from about −50 to about −1000 bp, usually from −50 to about −800, and more specifically from −50 to −500 bp from the transcription initiation codon. The enhancer element can be located upstream or downstream in relation to the promoter it affects. Alternatively, the enhancer element may be positioned within introns in the transcription unit.

The enhancer elements of the present invention specifically comprise the following fragments:

A: corresponding to a polynucleotide molecule having the sequence between positions −147 to −158 (SEQ ID NO: 1).

B: corresponding to a polynucleotide molecule having the sequence between positions −159 to −181 (SEQ ID NO: 2)-; and C: corresponding to a polynucleotide molecule having the sequence between positions −182 to −197 (SEQ ID NO:3).

These enhancer elements are separately functional, cis-acting elements, and each individually, in tandem, or dispersed, is independently capable of affecting gene transcription of a promoter operatively linked thereto.

According to a preferred embodiment, these enhancer elements may be variously combined to provide synergistic effect in increasing the gene transcription capabilities of a promoter operatively linked to these elements. Likewise, those enhancer elements may be variously combined to confer regulatable control to an operably linked gene.

The enhancer elements may be used independently, or in various combinations, or repeated, for example, five times. The elements may be linked to each other in direct repeats or in inverted repeats.

The enhancer elements described herein can be isolated from natural sources (e.g., tobacco) or can be synthesized by standard DNA synthesis techniques. See for example, Current Protocols in Molecular Biology, Unit 2.11, Ausubel, et al. Eds, (John Wiley & Sons 1995).

In one embodiment, the enhancer elements according to the instant invention have the general formula (I):

wherein A, B, and C are defined as above, and P comprises a native or non-native minimal promoter; wherein A, B, C and P are operatively linked to each other and may be in any order; and wherein l, m, n are independent of each other and may be any integer between 0–5, provided that l, m and n are not simultaneously zero; and provided that the naturally-occurring configuration of the rpL34 promoter is excluded.

In a preferred embodiment, the enhancer elements according to the instant invention have the general formula (II):

wherein A, B, C, l, m, n and P are as defined as in Formula (I), q is any integer between 1–5 provided that the naturally-occurring configuration of the rpL34 promoter is excluded.

Specific embodiments of formulae I and II include, but are not limited to 5'-A-P-3' (SEQ ID NO:5), 5'-A-A-P-3' (SEQ ID NO:6), 5'-A-A-A-A-A-P-3' (SEQ ID NO:7), 5'-B-P-3' (SEQ ID NO: 8), 5'-B-B-P-3' (SEQ ID NO:9), 5'B-B-B-P-3' (SEQ ID NO:10), 5'-C-C-C-C-P-3' (SEQ ID NO:11), 5'-A-B-P-3' (SEQ ID NO:12), 5'-A-B-A-B-P-3' (SEQ ID NO:13), 5'-A-B-A-B-A-B-P-3' (SEQ ID NO: 14); 5'-A-B-C-P-3' (SEQ ID NO: 15), 5'-A-B-C-A-B-C-P-3' (SEQ ID NO: 16) and 5'-A-B-C-A-B-C-A-B-C-P-3' (SEQ ID NO:17).

3. Promoter-enhancer combinations

In a preferred embodiment, the enhancer elements of the present invention are operatively linked to a promoter without affecting the intrinsic specificity of the promoter. Suitable promoters include any plant-compatible promoter.

The promoters suitable for the invention may be a native promoter (i.e. the rpL34 promoter itself) or a non-native promoter element. A "non-native" promoter is any plant-compatible promoter other than the tobacco rpL34 promoter. The expression of structural genes employed in the present invention may be operably linked to the unique promoters described herein. Preferably, the promoter is a non-native regulatory sequence in relation to the gene of interest.

For plant expression vectors, suitable viral promoters include the 35S RNA and 19S RNA promoters of CaMV (Brisson et al., Nature 310:511, (1984); Odell et al., Nature 313:810 (1985); the full-length transcript promoter from Figwort Mosaic Virus (FMV) (Gowda et al., J. Cell Biochem. 13D: 301 (1989)) and the coat protein promoter from TMV (Takamatsu et al., EMBO J. 6:307 (1987)). Alternatively, plant promoters such as the light-inducible promoter from the small subunit of ribulose bis-phosphate carboxylase (ssRUBISCO) (Coruzzi et al., EMBO J. 3:1671, (1984); Broglie et al., Science 224:838 (1984); mannopine synthase promoter (Velten et al., EMBO J. 3:2723 (1984) nopaline synthase (nos) and octopine synthase (ocs) promoters (carried on tumor-inducing plasmids of Agrobacterium tumefaciens) or heat shock promoters, e.g., soybean hsp17.5-E or hsp17.3-B (Gurley et al., Mol. Cell. Biol. 6:559 (1986); Severin et al., Plant Mol. Biol. 15:827 (1990) may be used.

Promoters useful in the invention include both constitutive, tissue-preferred or inducible promoters. These promoters may have the nucleotide sequence found in nature or comprise altered nucleotide sequences. A gene under the control of a constitutive promoter is expressed constantly and the level of expression is largely determined by the strength of the promoter. The CaMV 35S promoter is an example of a largely constitutive promoter.

A gene under the control of an inducible promoter is expressed only in response to certain stimuli (an "inducer"), such as in response to an environmental condition or when the cell reaches a certain developmental stage. To be most useful, an inducible promoter should 1) provide no or low expression in the absence of the inducer; 2) provide high expression in the presence of the inducer; 3) employ an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett et al., Proc. Natl. Acad. Sci., U.S.A. 90:4567 (1993); In2-1 and In2-2 regulator sequences which are activated by substituted benzenesulfonamides, e.g., herbicide safeners (Hershey et al., Plant Mol. Biol. 17:679 (1991); and the GRE regulatory sequences which are induced by glucocorticoids (Schena et al., Proc. Natl. Acad. Sci., USA. 88:10421 (1991). Other promoters, both constitutive and inducible will be known to those of skill in the art.

The particular promoter selected should be capable of causing sufficient expression to result in the production of an effective amount of the protein encoded by the structural gene. The promoters used in the constructs of the present invention may be modified, if desired, to affect their control characteristics.

Environmentally regulated promoters, e.g., promoters regulated by light and drought may be utilized in the present invention. Hormonally regulated promoters may also be utilized. Examples of hormonally regulated promoters include those that transcribe some of the cereal α-amylase genes, (especially rice and barley α-amylase gene promoters), the sucrose synthase promoters and sucrose-6-phosphate-synthetase promoters.

Tissue-preferred promoters may also be utilized in the present invention. An example of a tissue-preferred promoter is the promoter expressed in shoot meristems (Atanassova et al., *Plant J* 2:291 (1992). Well known tissue-preferred promoters useful in transgenic plants, include fruit-specific and seed-specific promoters, or the cdc2a promoter and cyc07 promoters. (See, for example, Ito et al., *Plant Mol. Biol.* 24:863 (1994); Martinez et al., *Proc. Natl. Acad Sci. USA* 89:7360 (1992); Medford et al., *Plant Cell* 3:359 (1991); Terada et al., *Plant Journal* 3:241 (1993); Wissenbach et al., *Plant Journal* 4:411 (1993). The rpL34 promoter itself is know to be associated with cell division and is meristem specific. See, e.g., Example 3, infra.

As discussed above, the enhancer elements of the instant invention, when operably linked to the promoter, may not alter the pattern of expression of the promoter. The enhancer element(s) of the instant invention increase the level of expression of the promoter to which the elements of the instant invention may alter the pattern of expression of the promoter to which they are operably linked. Alternatively, the enhancers are operably linked.

4. Structural Genes

The promoter, in turn, is operably linked to a gene of interest. The gene usually includes an open reading frame (ORF) encoding a polypeptide or protein having the desired biological activity. Methods for obtaining such genes are well-known to those skilled in the art. For example, open reading frames may be from natural open reading frames encoding protein products, cDNA sequences, synthetic DNA, open reading frames derived from exon ligation, or combinations thereof.

Genes whose level of expression may be increased according to the present invention include, but are not limited to, sequences from the natural genes (plant, animal, bacterial, viral, fungal) which encode primary RNA products; synthetic DNA sequences which encode a specific RNA or protein product; DNA sequences modified by mutagenesis, for example site specific mutagenesis; chimeras of any of the above (to produce fusion proteins); and DNA sequences encoding complementary RNA molecules (antisense), and combinations and/or fragments of the above.

Examples of proteins that can be produced at increased levels utilizing the present invention include, but are not limited to pharmaceuticals; nutritionally important proteins; growth promoting factors; proteins for early flowering in plants; proteins giving protection to the plant under certain environmental conditions, e.g., proteins conferring resistance to metals or other toxic substances, such as herbicides or pesticides; stress related proteins which confer tolerance to temperature extremes; proteins conferring resistance to fungi, bacteria, viruses, insects and nematodes; proteins of specific commercial value, e.g., enzymes involved in metabolic pathways, such as EPSP synthase.

5. Method

In one embodiment, the invention provides a method for increasing expression of a gene in a cell. The method includes operably linking an enhancer element, according to the present invention, to a promoter which is operably linked to a gene of interest. The enhancer element increases the expression of the gene. The promoter can be constitutive or inducible. The terms "increased" or "increasing" as used herein refer to gene expression which is elevated as compared to expression of the corresponding wild type gene that is not associated with a promoter containing an enhancer element according to the present invention.

The present invention also provides an rpL34 minimal promoter, which comprises the nucleotide sequence of +35 to –128 of FIG. 10. The specifics of the rpL34 minimal promoter are described in FIG. 2.

6. Markers and Vectors

The enhancer elements according to the present invention are especially suitable for the construction of gene expression vectors. Methods for preparing gene expression vectors are well known to those skilled in the art. For example, the expression vector may be a plasmid into which the gene, under the control of a suitable promoter and other regulatory elements, and encoding a product of interest, has been inserted.

Optionally, a selectable marker may be associated with the construct containing the enhancer element and the structural gene operatively linked to a promoter. As used herein, the term "marker" refers to a gene encoding a trait or a phenotype which permits the selection of, or the screening for, a plant or plant cell containing the marker. Preferably, the marker gene is an antibiotic resistance gene whereby the appropriate antibiotic can be used to select for transformed plant cells from among cells that are not transformed. Examples of suitable selectable markers include adenosine deaminase, dihydrofolate reductase, hygromycin-B-phosphotransferase, thymidine kinase, xanthine-guanine phosphoribosyltransferase and amino-glycoside 3'-O-phosphotransferase II (kanamycin, neomycin and G418 resistance). Other suitable markers will be known to those of skill in the art. For example, screenable markers, such as the uidA gene, GUS, luciferase or the GFP gene may also be used.

7. Transgenic Plants

Also disclosed are transgenic plants comprising the enhancer elements. The enhancer elements according to the present invention may be used in the same or different species from which it is derived or in which it naturally functions. More preferably, the enhancer element is used for enhanced gene expression in plants. Most preferably, the enhancer elements according to the present invention is used for non-native gene expression in a plant. By "non-native" gene expression it is meant that the enhancer elements, and the promoter operatively linked thereto, controls and enables high level expression of a gene that is not normally found in the host plant.

The transformation of plants in accordance with the invention may be carried out in essentially any of the various ways known to those skilled in the art of plant molecular biology. (See, for example, Methods of Enzymology, Vol. 153, 1987, Wu and Grossman, Eds., Academic Press, incorporated herein by reference). As used herein, the term "transformation" refers to alteration of the genotype of a host plant by the introduction of exogenous or endogenous nucleic acid sequences.

To commence a transformation process in accordance with the present invention, it is first necessary to construct a suitable vector and properly introduce the vector into the plant cell. The details of the construction of the vectors utilized herein are known to those skilled in the art of plant genetic engineering.

For example, the enhancer-promoter constructs utilized in the present invention can be introduced into plant cells using Ti plasmids, root-inducing (Ri) plasmids, and plant virus vectors. For reviews of such techniques see, for example, Weissbach & Weissbach, 1988, Methods for Plant Molecular Biology, Academic Press, N.Y., Section VIII, pp. 421–463; and Grierson & Corey, 1988, Plant Molecular Biology, 2d Ed., Blackie, London, Ch. 7–9, and Florsch et al., *Science* 227:1229 (1985), both incorporated herein by reference.

One of skill in the art will be able to select an appropriate vector for introducing the nucleic acid sequences of the invention in a relatively intact state. Thus, any vector which will produce a plant carrying the introduced DNA sequence should be sufficient. Even a naked piece of DNA would be expected to be able to confer the properties of this invention, though at low efficiency. The selection of the vector, or whether to use a vector, is typically guided by the method of transformation selected.

For example, a heterologous nucleic acid sequence can be introduced into a plant cell utilizing *Agrobacterium tumefaciens* containing the Ti plasmid. When using an *A. tumefaciens* culture as a transformation vehicle, it is most advantageous to use a non-oncogenic strain of the Agrobacterium as the vector carrier so that normal non-oncogenic differentiation of the transformed tissues is possible. It is also preferred that the Agrobacterium harbor a binary Ti plasmid system. Such a binary system comprises 1) a first Ti plasmid having a virulence region essential for the introduction of transfer DNA (T-DNA) into plants, and 2) a chimeric plasmid. The chimeric plasmid contains at least one border region of the T-DNA region of a wild-type Ti plasmid flanking the nucleic acid to be transferred. Binary Ti plasmid systems have been shown effective to transform plant cells (De Framond, *Biotechnology*, 1:262, 1983; Hoekema et al., *Nature* 303:179 (1983). Such a binary system is preferred because it does not require integration into Ti plasmid in Agrobacterium.

Methods involving the use of Agrobacterium include, but are not limited to: 1) co-cultivation of Agrobacterium with cultured isolated protoplasts; 2) transformation of plant cells or tissues with Agrobacterium; or 3) transformation of seeds, apices or meristems with Agrobacterium.

In addition, gene transfer can be accomplished by in situ transformation by Agrobacterium, as described by Bechtold et al., C. R. *Acad Sci. Paris* 316:1194 (1993). This approach is based on the vacuum infiltration of a suspension of Agrobacterium cells.

Alternatively, the enhancer construct described herein can be introduced into a plant cell by contacting the plant cell using mechanical or chemical means. For example, nucleic acid can be mechanically transferred by direct microinjection into plant cells utilizing micropipettes. Moreover, the nucleic acid may be transferred into plant cells using polyethylene glycol which forms a precipitation complex with genetic material that is taken up by the cell.

The nucleic acid can also be introduced into plant cells by electroporation (Fromm et al., *Proc. Natl. Acad. Sci., U.S.A.* 82:5824 (1985), which is incorporated herein by reference). In this technique, plant protoplasts are electroporated in the presence of vectors or nucleic acids containing the relevant nucleic acid sequences. Electrical impulses of high field strength reversibly permeabilize plant membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing nucleic acid into a plant cell is high velocity ballistic penetration by small particles with the nucleic acid to be introduced contained either within the matrix of small beads or particles, or on the surface thereof (Klein et al., *Nature* 327:70 (1987). Although, typically only a single introduction of a new nucleic acid sequence is required, this method particularly provides for multiple introductions. Cauliflower mosaic virus (CaMV) may also be used as a vector for introducing heterologous nucleic acid into plant cells (U.S. Pat. No. 4,407,956). The CaMV viral DNA genome is inserted into a parent bacterial plasmid creating a recombinant DNA molecule which can be propagated in bacteria. After cloning, the recombinant plasmid may be re-cloned and further modified by introduction of the desired nucleic acid sequence. The modified viral portion of the recombinant plasmid is then excised from the parent bacterial plasmid, and used to inoculate the plant cells or plants.

8. Production of Proteins Using Transgenic Plants

The vectors of this invention can be used to facilitate the expression and/or secretion of heterologous proteins in cell culture or by crop cultivation.

Plant cells comprising an expression vector for high level expression of the protein product of interest, are placed and maintained in suspension culture, and induced through the variety of inducers, suitable for the promoters used to construct the expression vectors described above, to produce high levels of the desired heterologous protein. The protein is then isolated using conventional technology.

Alternatively, plant cells comprising the expression vector for high level expression of the protein of interest, may be regenerated into transgenic plants as described above. Suitable plant parts of the plant are then harvested and the protein product isolated using conventional technology.

Because the purification steps differ from protein to protein, it is sufficient to indicate that the initial purification process typically will be similar to the purification process for the native protein from its host. Because the growth media of the plant suspension culture, as used in the present invention, is typically more simple than the normal host environment of the protein of interest, the purification procedures may be appropriately modified and simplified by those of skill in the art.

It is evident from the above results, that plant cells can be engineered and the cells used to propagate plants. The plant cells can be modified to provide for expression constructs that allow controlled expression of the coding sequence. By combining the technology of the present invention with well-established production methods (e.g., plant cell fermentation, crop cultivation, and product recovery), recombinant protein can be efficiently and economically produced for the biopharmaceutical, industrial processing, animal health and bioremediation industries.

The following examples are given to illustrate the present invention. It should be understood that the invention is not to be limited to the specific conditions or details described in these examples. Throughout the specification, any and all references to publicly available documents are specifically incorporated by reference.

EXAMPLE 1

1.1 Physical Description of the rpL34 Promoter Region

Figure 1:
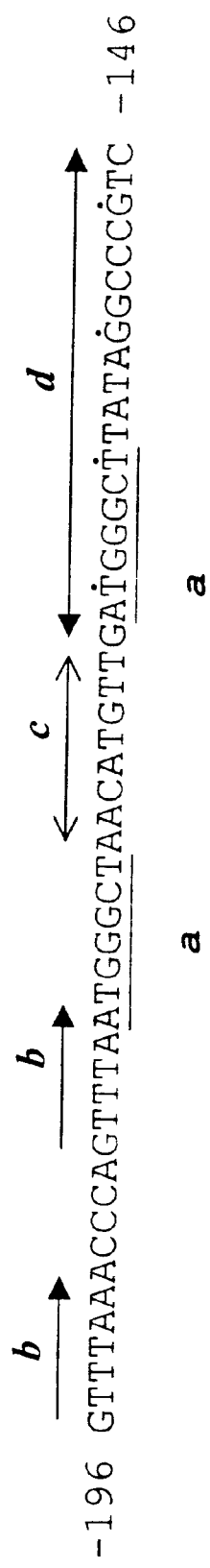
FIG. 1. DNA sequence (SEQ ID NO:27) containing three cis-acting elements in the rpL34 promoter. The sequence is located between −196 and −146 upstream the transcriptional start site. The two pairs of perfect repeats are labeled as a and b. The two palindromes are labeled as c and d, respectively, where the mismatched base pair is annotated with a dot.

Previous 5' and 3' unidirectional deletion analyses of the rpL34 promoter showed that the promoter carries the consensus TATA box and CCAAT box sequences at −57 bp and −104 bp relative to upstream the putative transcriptional start point. In addition, a 50-bp DNA region located between −179 bp and −129 bp is required for gene expression and for auxin, cytokinin, and wound responses. Dai et al., *Plant Mol Biol* 32:1055–1065 (1996). FIG. 1 gives the DNA sequence of the region between −196 to −146 from the transcription start site. Sequence analysis of this region reveals a few interesting characteristic features (FIG. 1). There are two 7-bp perfect repeat elements designated a (ATGGGCT, located between −180 to −174 and between −164 to −158) and two 6-bp perfect repeat elements designated b (GTTTAA, located between −196 to −191 and between −185 and −180). These two pairs of repeats are next to each other. In addition, there are two palindromes located in close proximity to each other. One is an 8-bp perfect palindrome element designated c (5' AACA⇑TGTT 3', located between −173 to −166) located between a repeats, while the other is a 20-bp palindrome element designated d (5' GA<u>T</u>GGGC TTA⇑TA<u>G</u>GCCC<u>G</u>TC 3' (SEQ ID NO:18), located between −165 to −146). The downstream a element was embedded in the d palindrome. These palindrome DNA elements can potentially form secondary stem-loop structures, which could play a possible regulatory role in gene expression. The significance of these DNA fragments will be discussed below.

EXAMPLE 2

This example describes the materials and strategies used for gene cloning, protoplast transient assays and stable transformation assays of the expression of a reporter gene under the control of the tobacco rpL34 promoter. Use of this system enables one to study the function of either inserted or deleted sequences operably linked to the reporter gene in terms of transcriptional activity.

2.1 Bacterial Strains and Plant Materials

*Escherichia coli* DH5α was used as the host for routine cloning experiments. The *Agrobacterium tumefaciens* strain PC2760 was the host for the binary vectors and transformation of *Nicotiana tabacum* cv SR1. *Nicotiana tabacum* cell suspension culture designated NT1 was used for electroporation experiments.

2.2 Transient and Stable Transformation in Tobacco

The electroporation of tobacco protoplasts was performed as described in Ebert et al., *Proc Natl Acad Sci USA* 84:5745–5749 (1987) with slight modifications. Test DNA (20 μg) and carrier DNA (10 μg) were used in each electroporation. The protoplasts were incubated in the dark at 28° C. for 45 h before they were collected for protein extraction and MUG assays. The HindIII/SacI promoter-GUS reporter fragments in pBI221 were inserted into the plant expression vector pGA482. An et al., "Binary vectors" in *Plant Molecular Biology Manual,* Gelvin and Schilperoort Eds. (Kluwer Academic Publishers, Dordrecht, Netherlands 1988), pages A3/1–19. Transformation of these constructs based on pGA482 into *Agrobacterium tumefaciens* strain CP2670 was conducted by the freeze-and-thaw method as described by Ebert et al., *Proc Natl Acad Sci USA* 84:5745–5749 (1987). Plasmid DNA from the transformed Agrobacterium clones was isolated and digested with various specific restriction enzymes and analyzed in agarose gel to confirm transformation of each construct. Tobacco leaf disc transformation and plant regeneration were performed as described by An et al., *Meth Enzymol* 153:293–305 (1987). At least 15 independently transformed plants were regenerated for each promoter construct that was described earlier. $T_1$ seeds were collected and grown under sterile conditions on agar media containing MS (Murashige and Skoog, 1962, *Physiol. Plant* 15:473–497) with 50 μg ml$^{-1}$ kanamycin and 250 μg ml$^{-1}$ cefotaxin. Kanamycin resistant $T_1$ seedlings were selected, transferred to soil and grown to maturity.

2.3 Fluorometric and Histochemical Analysis of GUS Activity

For histochemical staining, regenerated plants were allowed to self pollinate. Surface sterilized $T_1$ seeds were germinated on MS medium containing 50 μg/ml kanamycin and 250 μg/ml cefetaxin. Different development stages of plants, seeds or longitudinally excised flowers were collected and histochemically analyzed as described by Dai et al., *Plant Mol Biol* 32:1055–1065 (1996).

Fluorometric quantitation of GUS activity was performed according to Jefferson et al., *EMBO J* 6:3901–3907 (1987). Fresh young leaves of independent transgenic tobacco were ground in lysis buffer (50 mM sodium phosphate, pH 7.0. 10 mM EDTA, 0.1% TritonX-100, 0.1% sarkosyl and 10 mM DTT). Tobacco protoplast protein was extracted in the same buffer by sonication on ice twice, 5 seconds each time. Protein concentrations were determined by the Bio-Rad method (Bradford 1976 Anal Biochem 72:248–254). Approximately 5–10 μg of protein was incubated in the presence of 1 mM 4-methylumbelliferyl β-D-glucuronide in 100 μl of lysis buffer at 37 C. Samples from each reaction were taken at 0, 15, and 30 min intervals and the enzyme reaction was quenched in 0.2 M sodium carbonate ($Na_2CO_3$). The flurometer was calibrated with 100, 200, 300, and 400 nM 4-methylumbelliferon in 0.2M sodium carbonate.

EXAMPLE 3

This example details the experimental steps of internal deletion analysis that were used in the identification of the enhancer elements of the rpL34 promoter, as well as data showing that the native rpL34 promoter is tightly linked with cell division. The examples describe the steps taken to prepare the internal deletion of rpL34 promoter fused to GUS reporter gene with the 3' nos terminator. The loss-of-function analysis of these mutant promoters in terms of transcriptional activity was performed in both transient assays and stable transformation assays. Histochemical GUS staining of transgenic tobacco enables us to observe the spatial and temporal expression patterns of the rpL34 promoter.

3.1 Construction of rp134 Internal Deletion Promoter/GUS Fusion Genes

Internal deletion constructs were prepared either by restriction enzyme digestion (constructs −1500, Δ128, and Δ438) or polymerase chain reaction (PCR) methods (constructs Δ147, Δ159, Δ175, Δ185, Δ196, and Δ210). A 1.5-kb flanking region of rpL34 starting from 8 nucleotides upstream of the putative translational start codon was excised by digestion with restriction enzymes (HindIII and BamHI) and inserted into the same sites of pBluescript SK (−) vector, producing pGA1241-10. The BamHI-EcoRI (filled-in) fragment containing the GUS reporter gene (uidA gene for *Escherichia coli* β-glucronidase) and nopaline synthase (nos) terminator of pBI221 was inserted into the BamHI/SacII (blunt end) sites of the plasmid, generating construct −1500 (the full length rpL34 promoter-GUS-nos cassette in SK). The larger fragments from digestion of construct −1500 with SpeI (cuts at −128)/Bgl II (cuts at −438) containing the GUS gene, 3' terminator and vector sequences was isolated, treated with the Klenow fragments, and self-ligated, producing construct Δ−438. The minimal promoter construct (Δ128) was prepared by digestion of construct −1500 with SpeI (cuts at −128)/HindIII(cuts at −1500).

Six additional constructs with internal deletions of various lengths were prepared by PCR. Six 3' PCR primers were synthesized corresponding to the specific region of the rpL34 promoter with an attached 5'-end SpeI site. PCR was conducted with each of these six primers and one 5' primer complementary to the cloning vector beyond the polylinker cloning site served as the opposing primer using pGA1241-10 as the DNA template. Subsequently, amplified products digested with HindIII (from the cloning vector) and SpeI were used to replace the region between the HindIII and the SpeI sites of the full-length promoter in construct −1500. The preparation of construct m178, where A was mutated to G, and Δ181/147, where the region between −181 and −147 was deleted, is described in Example 4.

3.2 Internal Deletion Analysis of the rpL34 Promoter

Figure 2A:
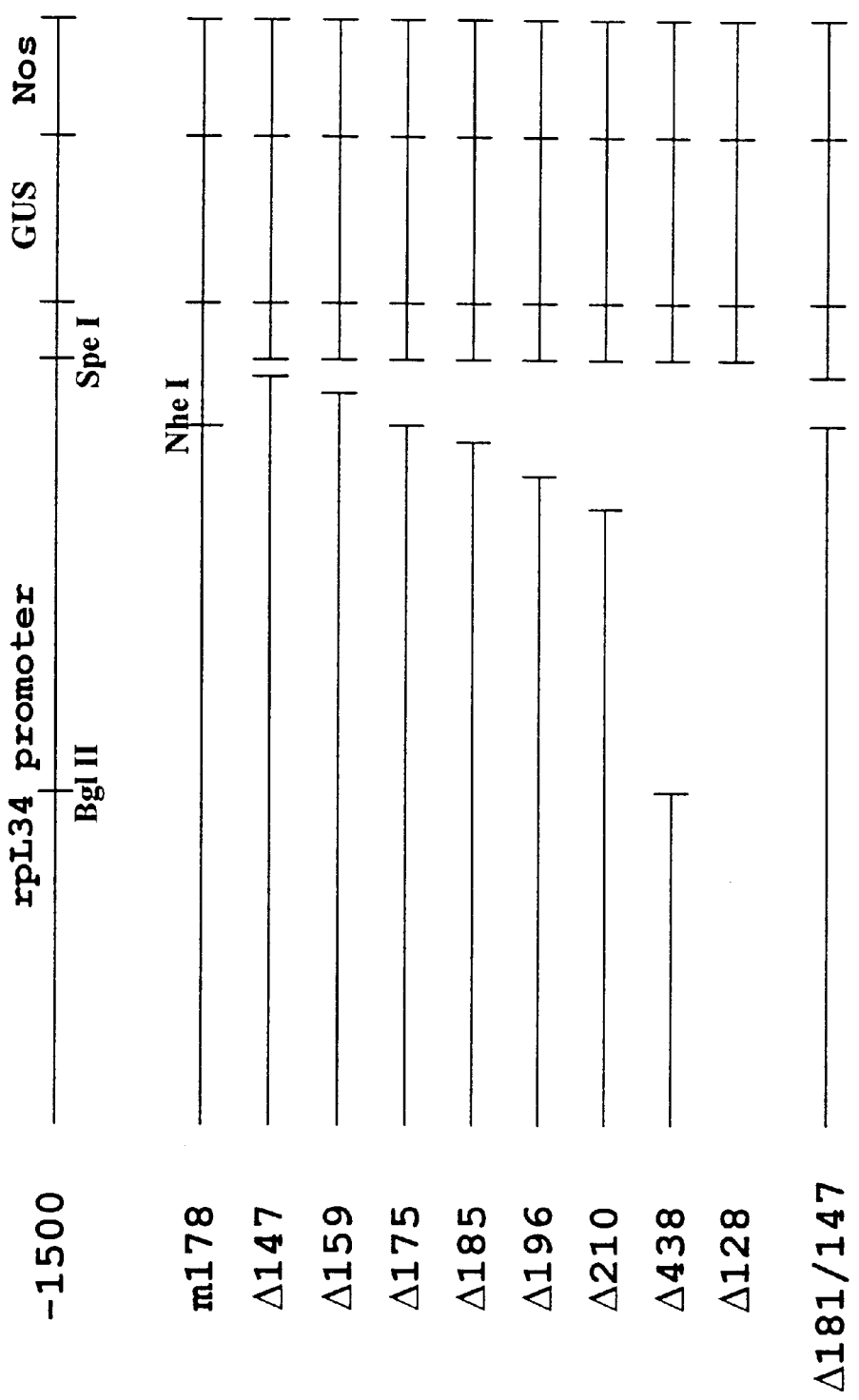
FIGS. 2a–2c. Internal deletion analysis of the rpL34 promoter.

To further define the precise sequence(s) controlling the gene expression of rpL34, a series of internal deletion derivatives of the rpL34 promoter fused to the β-glucuronidase (GUS) gene (Jefferson et al., *EMBO J* 6:3901–3907 (1987) were created in the loss-of-function analysis. A schematic diagram illustrating the series of internally deleted mutants of the rpL34 promoter is shown in FIG. 2a. The full length rpL34 promoter (−1500) and its 5' minimal promoter (Δ128) were used as controls. We initially examined the promoter activity in tobacco transient assays, because the rpL34 promoter is active in protoplasts. Transient assays of each construct for GUS activity can be obtained more easily and rapidly than the stable transformation. Moreover, it has been established that transient GUS activity in protoplasts is predictive of GUS activity in stably transformed plants. Dai et al., *Plant Mol Biol* 32:1055–1065 (1996).

Figure 2B:
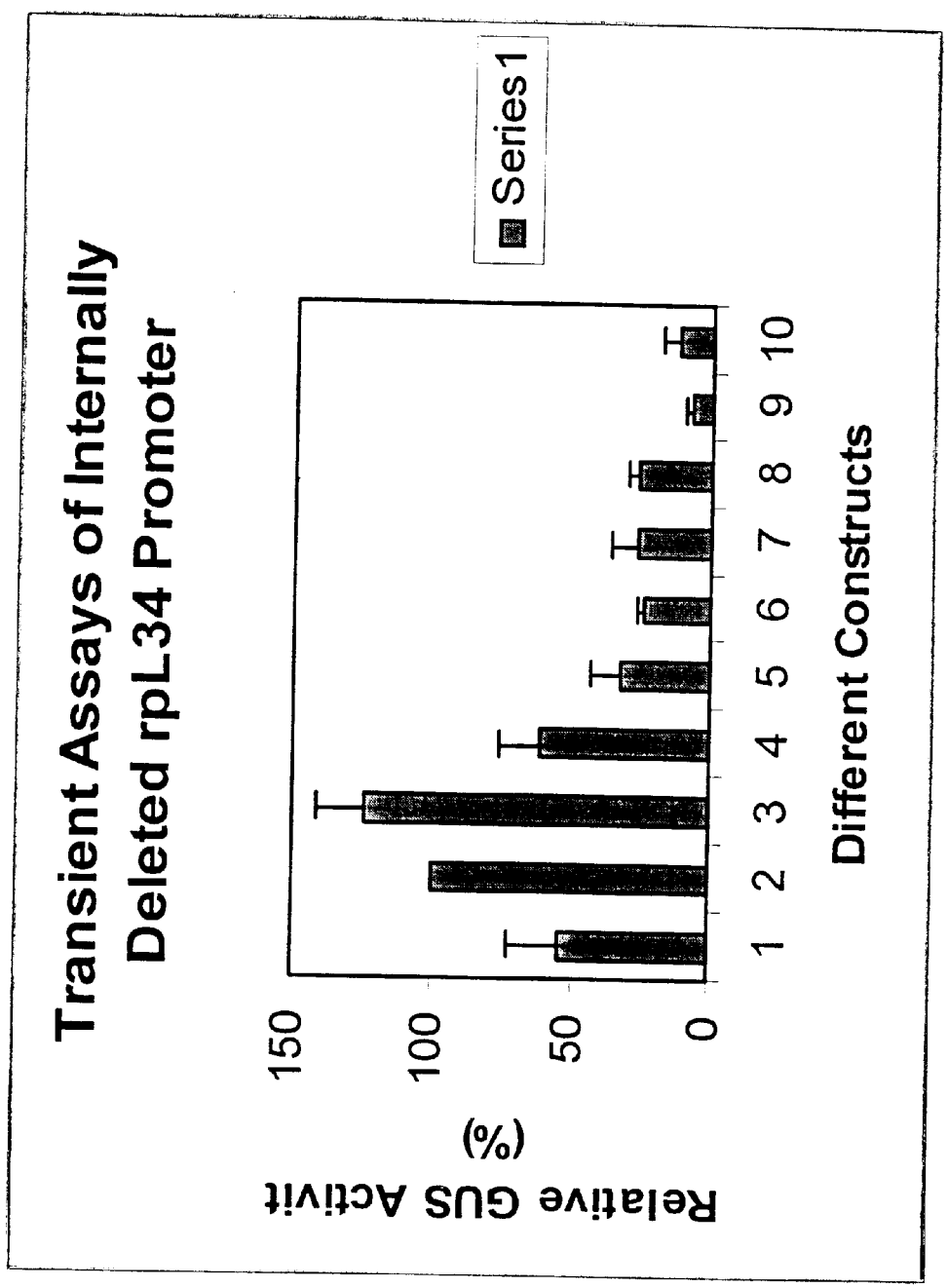

Each construct was transfected into tobacco protoplast by electroporation, and GUS activity was assayed 2 days later. Transient assays were repeated 3–6 times for each construct to minimize experimental error and allow meaningful comparisons of the relative GUS activities. In comparison to the full length of rpL34 promoter (−1500), a slight increase in the level of the GUS activity consistently was detected when the region between −128 to −147 was deleted (FIG. 2b). This may be due to the shortened distance between the cis-element(s) and the TATA box and CCAAT box in the promoter. An additional 12 bp deletion extending to −159 resulted in significantly decreased GUS activity. With further deletion to −175 and −185, there was a corresponding decrease in GUS activity. However, no significant decrease in GUS activity was detectable, as the deletion was further extended to −196 and −210. When the region between −128 to −348 or −1500 to −128 was deleted, very little GUS activity was observed. The GUS activity was completely undetectable in transgenic plants containing the −128 minimal promoter (FIG. 2b). Further, when the region between −147 to −181 was deleted, the rpL34 promoter showed undetectable GUS activity (FIGS. 4N, 5N and 6C), indicating the presence of cis-element(s) in the region between −147 to −181. These results indicate the presence of, at least, one regulatory element in the rpL34 promoter.

Figure 2C:
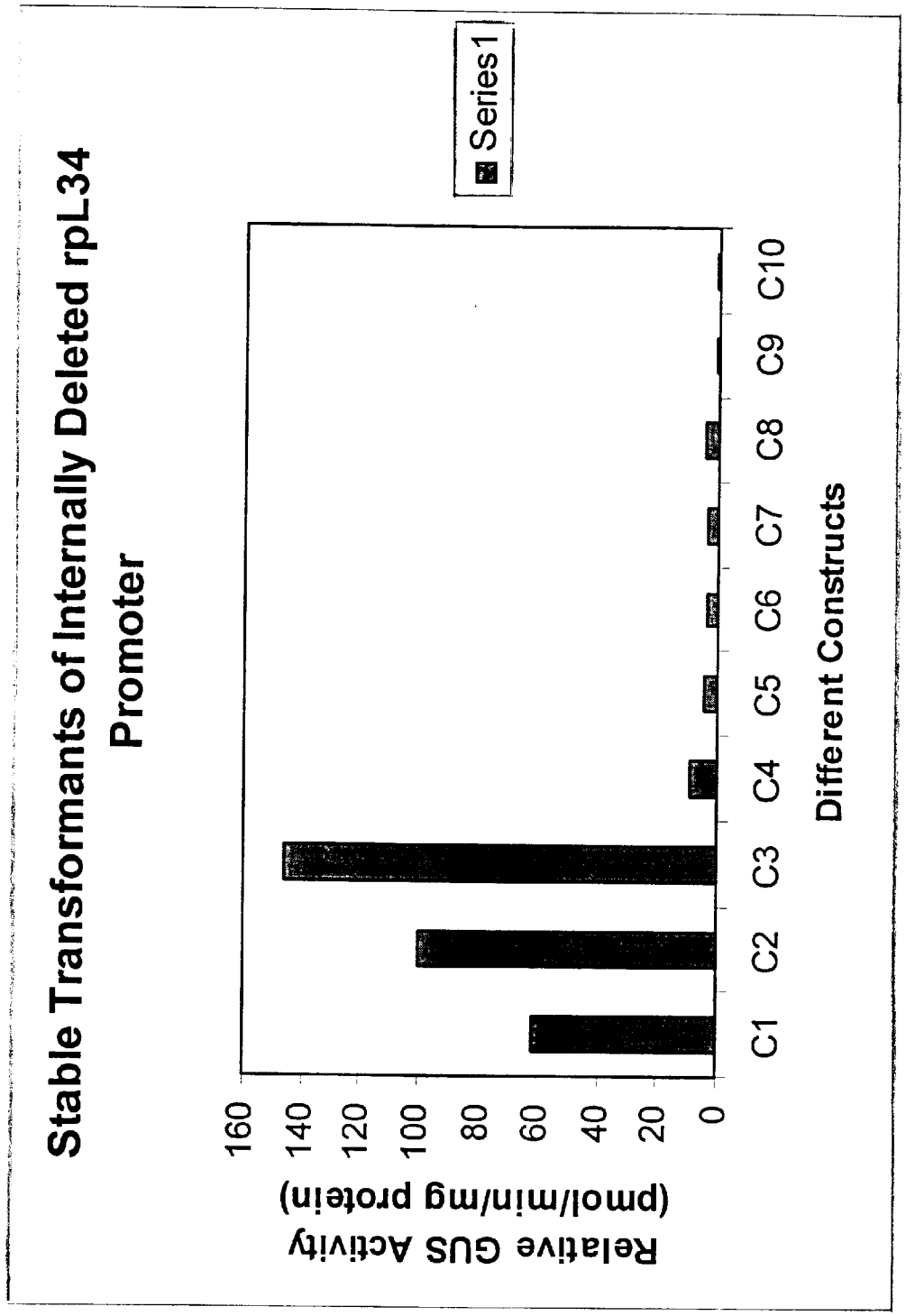

Each rpL34 internal deletion construct was stably transformed into tobacco and GUS activity was assayed for 14–22 independent transgenic lines. The large number of lines sampled for each construct was used to minimize variability among lines due to insert position and copy number and to allow meaningful comparisons of the average levels of GUS expression in leaves. A slight increase in the level of the GUS activity was detected when the region between −128 to −147 was deleted as shown in FIG. 2c. In transgenic tobacco GUS activity significantly decreased when the region between −128 and −159 was deleted. With further deletion to −175 and −185, there is a corresponding decrease in GUS activity. The results from the analysis of stable transgenic tobacco support the presence of important regulatory element(s) between −147 bp and −185 bp. The results in transgenic plants are consistent with that in transient assays (FIGS. 2b and 2c), except that the residual level of GUS activity is slightly higher in transient analyses.

3.3 Histochemical Analysis of the Internal Deletion Constructs of rpL34 Promoter Previous in situ hybridization and promoter analyses showed that the expression of rpL34 proceeded in a meristem-specific manner (Gao et al., *Plant Mol Biol* 25:761–770 (1994) and Dai et al., *Plant Mol Biol* 32:1055–1065 (1996). In order to understand the transcriptional regulation of the cis-element(s) of the rpL34 gene, transgenic tobacco carrying the internal deletion promoters were examined in detail via histochemical GUS analysis. The spatial and temporal expression patterns of these chimeric genes were analyzed during plant growth and development. FIG. 3 shows the typical results of the histochemical analysis of GUS activity in transgenic tobacco plants. In accordance with previous data (Dai et al., *Plant Mol Biol* 32:1055–1065 (1996), in transgenic tobacco containing the full length of rpL34 promoter, GUS staining was strongly detected in the emerging meristem roots just 2 days after germination. In 4-day-old seedlings, strong GUS staining was observed in both cotyledons and roots. The shoot apical meristem at this stage still had a flat morphology. With further growth (at 6- and 16-day-old), GUS expression dramatically increased in the shoot apical meristem and remained high in the cotyledons. GUS staining in roots is mainly limited to root apical meristems (FIGS. 3B, 3G, 3J and 3Q). In 30-day-old seedlings, GUS staining was strongly detected in the shoot and root apical meristem. GUS staining was also found in leaf primordia and developing leaves but much less in fully expanded leaves (FIG. 4B). In mature flowers, intense GUS staining was found in the anthers, stigmas, transmitting tissues, and carpels, but not in the sepals and petals (FIG. 5B). These results indicate that the expression of rpL34 is tightly linked with cell division in tobacco and are consistent with the theory that protein synthesis is required for cell division. Among the internal deletion constructs, when the region between −128 and −147 was deleted, the pattern of GUS staining is similar to the wildtype promoter in seed germination and during seedling growth and development (FIGS. 3, 4 and 5). The intensity of GUS staining was dramatically decreased as the deletion extended from −147, to −158, −175, and −185, which corresponds very well with the GUS activity measured by fluorometric quantitation (FIGS. 3, 4 and 5). However, the location of GUS staining did not change, indicating that these cis elements are meristem specific. No GUS staining was detected in the roots and shoots through all stages of development when the regions between −128 and −196, −210, and −438 were deleted in transgenic tobacco. No GUS staining was detected in tissues containing −128 minimal promoter.

EXAMPLE 4

This example describes the steps taken to prepare the linker scanning mutation analysis of the rpL34 promoter fused to the GUS reporter gene with 3' nos terminator, to further identify the enhancer elements of the rpL34 promoter. This example provides further data showing that the native rpL34 promoter is tightly linked with cell division. The loss-of-function analyses of these mutated promoters in terms of transcriptional activity were performed in both transient assays and stable transformation assays. Histochemical GUS staining of transgenic tobacco enables one to study the spatial and temporal expression patterns of a reporter gene.

4.1 rpL34 Linker Scanning Mutation Promoter/GUS Fusion Genes

Five linker scanning mutation constructs (LS1 to LS5) of the rpL34 promoter were prepared using the 3-way PCR method according to White et al., "Directed mutagenesis and mutant analysis" in *Gene Probes,* Hames and Hinggis, Eds., (Oxford University Press, Walton Street, 1995), pages 329–355. These constructs consisted of targeted scanning mutation regions from −148 to −158, −158 to −171, −171 to −181, −181 to −191 or −158 to −181, respectively. In the first PCR, an oligonucleotide complementary to the 5'-end flanking region of the targeted sequence and containing a 5' attached PstI linker was synthesized and used as a 3' PCR primer. An oligonucleotide complementary to the cloning vector beyond the polylinker cloning sites served as the 5' opposing primer. In the second PCR, an oligonucleotide complementary to the 3'-end flanking region of the targeted sequence and containing a 5' attached PstI linker (which is complementary to the attached PstI linker in first PCR) was synthesized and used as a 5' PCR primer. An oligonucleotide complementary to the cloning vector beyond the polylinker cloning sites served as the 3' opposing primer. In the first two PCRs, pGA1241-10 was used as a DNA template. Subsequently, the two PCR products joined together by annealing the PstI linker region were used as a DNA template in the third PCR, in which the 5' primer from the first PCR and 3' primer from the second PCR flanking the cloning sites were used. The third PCR resulted in the replacement of the targeted sequence by the PstI linker as shown in FIG. 6a. Finally, the amplified PCR products (the full-length rpL34 with linker mutations) were digested with HindIII and SpeI and replaced the same region of the wild-type rpL34 promoter. Similarly, one base pair at position −178 of construct −1500 was mutated using two specific PCR primers including a NheI site where G was mutated to A, producing m178. The region of −147 to −181 was deleted, producing Δ147/181 as shown in FIG. 2a.

4.2 Linker-scanning Mutation Analysis of rpL34 Promoter

While a unidirectional or internal deletion analysis is capable of coarse characterization of regulatory regions in a promoter, linker-scanning mutagenesis permits a much higher resolution permitting identification of short, defined sequence motifs and their effect on promoter activity in terms of their relative location (McKnight and Kingsbury Science 217:316–324 (1982). We constructed a set of 5 linker-scanning mutants of the rpL34 promoter fused to GUS (LS1 to LS5, FIG. 6a). Each of them contained an 11–23 bp mutation located between position −147 and −191 and was embedded in the 1500 bp full-length promoter. The set of constructs was analyzed by both protoplast transient assays and stable transformation assays.

The effect of each mutation on promoter activity was assessed in comparison to that of the unmutated full-length promoter and its −128 minimal promoter. At least three independent experiments of transfection of the plasmids from each construct were carried out in tobacco protoplasts. LS1 (mutation at position −194 to −181) had approximately half of the full-length promoter activity. In LS2 (mutation at position −171 to −181), LS3 (mutation at position −159 to −170) and LS4 (mutation at position −147 to −158), a 70% to 80% loss of GUS activity was observed (FIG. 6b). A severe loss of GUS activity was observed in protoplasts containing LS5 (mutations at position −159 to −181). These results of the LS3, LS4 and LS5 analysis are consistent with the presence of at least one positive regulatory element that is necessary for the expression of rpL34 between positions −147 to −181.

The same set of constructs was also stably transformed into tobacco, and GUS activity for each construct was assayed in 14 to 42 independent transformants. The results were consistent with those from the transient assays (FIG. 6c). The pattern of GUS staining in transgenic tobacco containing LS1 is similar to that in the wild type promoter, with a decrease in its staining which is correlated with the measured GUS activity. A significant decrease in GUS activity and staining was observed in transgenic plants containing LS2, LS3, LS4 and LS5 (FIGS. 4 and 5).

EXAMPLE 5

This example describes the steps taken to prepare rpL34 promoter fragments upstream of the rpL34 minimal promoter fused to the GUS reporter gene with 3' nos terminator. The gain-of-function analyses of these mutated promoters in terms of transcriptional activity were performed in only transient assays. The results from this example demonstrate that the enhancer elements of the present invention may be combined with their native minimal promoter, in various repetitions, combinations and orientations, to achieve increased gene expression.

5.1 Preparation of rpL34 Promoter Fragments with its Minimal Promoter/GUS Fusion Genes One to several copies of rpL34 promoter fragment A (−147 to −158), B (−159 to −181), C (−182 to −197) or their combination was fused to the rp134 minimal promoter (Δ128) (FIG. 7a). Construct 5A was made using a 72-bp oligonucleotide (5'-AGCTT(TTATAGGCCCGTC)$_5$A-3' (SEQ ID NO:19), 5 copies of fragment A) and its complementary sequence (5'-CTAGT(GACGGGCCTATAA)$_5$A-3' (SEQ ID NO:20)). These two oligonucleotides were annealed, producing HindIII and SpeI sites, and inserted in the same sites of construct −1500 (FIG. 2). Construct 4C was prepared in the same way, except that the 75-bp oligonucleotide (5'-AGCTT(GTTTAAACCCAGTTTAA)$_4$A-3' (SEQ ID NO:21), 5 copies of fragment C) and its complementary sequence (5'-CTAGT(TTAAACTGGGTTTAAAC)$_4$A-3" (SEQ ID NO:22) were used. To prepare the additional constructs shown in FIG. 7a, oligonucleotides B, A+B, and A+B+C and their complementary sequences were annealed, producing BamHI and BgIII sites, multimerized, and inserted into BamHI digested SK vector. The cloned plasmid DNA was size screened and sequenced to confirm its orientation and copy number. These plasmids were then digested with HindIII and SpeI (both cuts in vector), producing 1–3 copies of rpL34 DNA fragments. Subsequently, these fragments were inserted into the HindIII SpeI sites of construct −1500, therefore being placed in front of the minimal rpL34 promoter with GUS reporter gene.

5.2 Gain-of-function Analysis of rpL34 cis-elements Fused with Their Own Minimal Promoter The loss-of-function analysis (internal deletion and linker scanning mutation) described above provides the evidence for the presence of multiple cis elements in the rpL34 promoter. Whether each of the cis-elements is independently functional and whether multiple elements are functionally separable was examined.

To perform the gain-of-function analysis, five different promoter fragments were fused to the minimal rpL34 promoter (Δ128)/GUS reporter gene (FIG. 7a). As described previously, single or multiple copies of the promoter fragments were fused to the minimal rpL34 promoter (Δ128)-GUS reporter gene. Due to the large number of constructs and consistent results from both transient and stable transformation in tobacco in the loss-of-function analyses described previously, the gain-of-function constructs were analyzed only in tobacco protoplast transient assays.

Results of these analyses are shown in FIG. 7b along with results from full length (−1500) and minimal promoter (Δ128) of rpL34 as controls. Insertion of one copy of the 50-bp fragment (A+B+C) in front of Δ128 in the reverse orientation resulted in a restored GUS activity. Two copies of the 50-bp fragment in tandem and normal orientation enhanced GUS activity 6 times more than −1500, indicating that this 50 bp contained cis-elements. When 5 copies of DNA fragment A located between −147 and −158 in the rpL34 promoter were fused to Δ128 in normal orientation of tandem repeats, GUS activity is restored 3 times higher than in −1500. When one copy of fragment B (−159 to −181) was fused with Δ128 in the reverse orientation, the GUS activity was also restored but not as much as two copies of fragment B. These results indicate that both fragment A and B can function as separable cis-elements in controlling the expression of rpL34. In addition, insertion of one or multiple copies of fragment A+B (−147 to −181) in Δ128 caused 3 to 12-fold increase in GUS activity, indicating that fragments A and B could function synergistically. In contrast, the construct containing four copies of fragment C in the normal orientation only restored 20% of the activity of −1500. In all, these results indicate that the rpL34 promoter consists of at least two cis-elements that could function independently of each other.

EXAMPLE 6

This example describes the steps taken to prepare rpL34 promoter fragments with the 35S minimal promoter fused to the GUS reporter gene with the 3' nos terminator. The gain-of-function analyses of these mutated promoters in terms of transcriptional activity were performed only using transient assays. The results from this example demonstrate that the enhancer elements of the present invention may be combined with other non-rpL34 promoters, in various repetitions, combinations and orientations, to achieve increased gene expression by the minimal promoter.

6.1 rpL34 Promoter Fragments with 35S CaMV (−46) Minimal Promoter/GUS Reporter Fusion Genes The 35S CaMV (−46) minimal promoter-GUS-nos cassette from X-GUS46 (Benfey et al., EMBO J 9:1677–1684 (1990) was excised by HindIII and EcoRI and inserted into the same sites of pUC19, producing pUC46GUS. Constructs 3B-35S, 3(A+B)-35S, or 2(A+B+C)-35S were produced by placing the HindIII/SacI fragments containing 2 to 3 copies of rpL34 DNA fragment B, A+B or A+B+C in front of the 35S CaMV (−46) minimal promoter-GUS-nos cassette in pUC46GUS. The HindIII/SacI fragments containing 4 or 5 copies of rpL34 DNA fragment A, or C, respectively, with rpL34 minimal promoter fused GUS reporter gene were excised from 5A-rpL34 and 4C-rpL34 and placed in front of the 35S CaMV (−46) minimal promoter-GUS-nos cassette in pUC46GUS. The DNA fragment carrying the rpL34 minimal promoter with GUS reporter gene was removed by restriction enzymes SpeI and SacI digestion followed by blunting ends and ligating, generating 5A-35S and 4C-35S.

6.2 Gain-of-function Analysis of rpL34 cis-elements Fused with 35S Minimal Promoter To study whether rpL34 cis-acting elements work independently with a foreign minimal promoter, the contribution of these DNA fragments to the minimal −46 CaMV 35S promoter is reported in terms of promoter activity. Only multiple copies of the DNA fragments were placed in front of the minimal −46 CaMV 35S promoter fused with GUS reporter gene (FIG. 8a). These constructs were introduced into tobacco protoplasts by electroporation and the GUS activity was measured 2 d after treatment. As shown in FIG. 8b, both 35S and rpL34 minimal promoters gave similar low levels of GUS activity. However, the full-length rpL34 promoter yields at least one fold higher activity than the full-length 35S promoter in the transient assays. Fragment C restored a little GUS activity in the minimal −46 CaMV 35S promoter, which is higher than that with its own rpL34 minimal promoter. The GUS activity was increased 2- to 3-fold when the minimal −46 CaMV 35S promoter was fused with either A or B DNA fragment. Interestingly, the fragment A+B made a similar contribution to the minimal 35S promoter as either an A fragment or a B fragment. In contrast, two copies of fragment A+B+C restored a larger GUS activity than three copies of fragments A+B, A or B. These results indicate that the DNA fragment A (−147 to −158) and fragment B (−159 to −181) act as an enhancer when fused with the minimal 35S promoter. However, these fragments preferably restore higher GUS activity when attached to their own native minimal promoter. Further, the Mac promoter, which is composed of the mannopine synthase (mas) promoter from the *Agrobacterium tumefaciens* octopine Ti plasmid) and the B-domain of the 35S promoter, showed the highest GUS activity among different constructs in the transient assays (FIG. 8b). Mac activity is approximately 5× higher than that of the full length rpL34 (−1500). The hybrid rpL34 3(A+B) (FIG. 7b) is approximately 12× higher than that of full length rpL34 (−1500). This indicates that hybrid rpL34 promoters may be more active than Mac in transient assay.

EXAMPLE 7

This example describes experiments performed to study the response of the rpL34 promoter to mechanical wounding and treatment with different plant hormones, such as 2,4-dichlorophenoxyacetic acid (2,4-D) and benzyladenine (BA). This analysis was performed using leaf discs excised from transgenic tobacco plants. The results from this example demonstrate that the enhancer elements of the present invention contribute to increased gene expression following wounding and the treatment with different hormones.

7.1 The Response of the rpL34 Promoter with Various Length of Deletion to Wounding and Plant Hormones Kanamycin resistant $T_1$ seedlings, each containing a unique internally deleted rpL34 promoter, were selected and grown to maturity. Six leaf discs excised from the fourth leaf of each plant by paper punch were randomly pooled and incubated in MS medium with 5 μM BA, 1 μM 2,4-D or no plant hormone (wounding treatment) for 24 hr at room temperature. Afterward, the materials were harvested and ground in protein extraction buffer as described in Example 2. The leaf discs ground immediately after excision in protein extraction buffer served as non-wounded tobacco controls. Fluorometric quantitation of GUS activity of each sample was performed as described in Example 2.

Previous promoter analyses showed that mechanical wounding increased the rpL34 promoter activity. This activity was further enhanced by plant growth regulators, such as, 2,4-D and BA (Dai et al., *Plant Mol Biol* 32:1055–1065 (1996)). The response of the rpL34 promoter, with various internal deletions, to wounding and plant hormones was further evaluated. As shown in FIG. 9a, GUS activities of each selected transgenic plant containing the full-length promoter (−1500 in lane 2), m178 (lane 1) or Δ147 (region of −147 and −128 deleted in lane 3) are shown. Mechanical wounding in leaf discs led to a higher GUS activity than in non-wounded leaf disks. Both 2,4-D and BA induced higher GUS activity than wounding alone in the same plant. In contrast, transformants containing the rpL34 promoter with one or more of the cis-acting elements deleted showed low GUS activities that were not increased following wounding and hormone treatment (Lanes 4–11 in FIG. 9). These results indicate that these cis-acting elements contribute to induction of GUS activity during wounding and treatment of plant cells with hormones.

We claim:

1. An enhancer element comprising an isolated polynucleotide molecule having the sequence of A which is −147 to −158 of FIG. 10 provided that the native configuration of the rpL34 promoter is excluded.

2. An enhancer element comprising an isolated polynucleotide molecule having the sequence of B which is −159 to −181 of FIG. 10 provided that the native configuration of the rpL34 promoter is excluded.

3. An enhancer element comprising an isolated polynucleotide molecule having the sequence which is −182 to −197 of FIG. 19 (SEQ ID NO:28) provided that the native configuration of the rpL34 promoter is excluded.

4. A recombinant promoter construct having the general formula (I) or (II):

$$[(A)_l, (B)_m, (C)_n, P] \quad (I)$$

or $$[(A)_l, (B)_m, (C)_n]_q, P \quad (II)$$

wherein
A is −147 to −158 of FIG. 10;
B −159 to −181 of FIG. 10;
C is −182 to −197 of FIG. 10; and
P is a native or non-native minimal promoter; wherein
A, B, C and P are operatively linked to each other and may be in any order; and wherein
l, m, n are independent of each other and may be any integer between 0–5, and q is any integer between 1–5, provided that l, m and n are not simultaneously zero; and provided that the native configuration of the rpL34 promoter is excluded.

5. The recombinant promoter construct according to claim 4, having the formula of 5'-(A-B-C)$_q$-P-3' wherein q is an integer between 1 and 3.

6. The recombinant promoter construct according to claim 4, having the formula of 5'-(A-B)$_q$-P-3', wherein q is an integer between 1 and 3, and wherein A-B may be inverted.

7. The recombinant promoter construct according to claim 4, having the formula of 5'-(A)$_q$-P-3', wherein q is an integer between 1 and 5, and wherein A may be inverted.

8. The recombinant promoter construct according to claim 4, having the formula of 5'-(B)$_q$-P-3', wherein q is an integer between 1 and 3 and wherein B may be inverted.

9. The recombinant promoter construct according to claim 4, wherein P is selected from the group consisting of a constitutive promoter, a tissue-specific promoter and an inducible promoter.

10. The recombinant promoter construct according to claim 9, wherein the inducible promoter is regulated by environmental factors or by developmental stages.

11. The recombinant promoter construct according to claim 9, wherein the promoter is selected from the group consisting of mannopine synthase, CaMV 35S or 19S, rubisco (RbcS-3C), chlorophyll a/b binding protein promoter (cab), nopaline synthase (nos), raspberry drupelet protein 1 promoter (druI), and *Arabidopsis thaliana* senescence associated gene SAG12 promoter.

12. A recombinant expression vector, comprising the recombinant construct according to claim 4, and a structural gene encoding a protein or RNA product.

13. A recombinant expression vector according to claim 12, further comprising a selectable marker.

14. A plant cell comprising the expression vector of claim 12.

15. A transgenic plant regenerated from the cell according to claim 14.

16. A method for producing a protein of interest comprising (1) obtaining a transgenic plant according to claim 14; (2) growing said plant; (3) harvesting the plant part that accumulates a recombinant expression product; and (4) extract and purify said expression product.

* * * * *

UNITED STATES PATENT AND TRADEMARK OFFICE
CERTIFICATE OF CORRECTION

PATENT NO. : 6,355,864 B1
DATED : March 12, 2002
INVENTOR(S) : Lifang Shi et al.

It is certified that error appears in the above-identified patent and that said Letters Patent is hereby corrected as shown below:

Title page,
Item [56], OTHER PUBLICATIONS, replace "al Promoter" with -- al.: "Promoter --; and replace "L34," with -- L34" --; and replace "reulated" with -- regulated --; and replace "Expression f a" with -- Expression of a--; and replace "deliving" with -- delivering --.

Column 1,
Line 59, replace "effect" with -- affect --.

Column 2,
Line 40, replace "is" with -- are --.

Column 7,
Line 20, replace "1)" with -- 1); --.

Column 13,
Line 60, replace "Agrobacterium" with -- *Agrobacterium* --.

Column 14,
Line 29, replace "flurometer" with -- fluorometer --.
Line 34, replace "rpl34" with -- rpL34 --.

UNITED STATES PATENT AND TRADEMARK OFFICE
CERTIFICATE OF CORRECTION

PATENT NO. : 6,355,864 B1
DATED : March 12, 2002
INVENTOR(S) : Lifang Shi et al.

It is certified that error appears in the above-identified patent and that said Letters Patent is hereby corrected as shown below:

Column 18,
Line 5, replace "analysis" with -- analyses --.
Line 34, replace "rpl34" with -- rpL34 --.

Signed and Sealed this

Twenty-second Day of April, 2003

JAMES E. ROGAN
*Director of the United States Patent and Trademark Office*

SEQUENCE LISTING

```
<160> NUMBER OF SEQ ID NOS:  28

<210> SEQ ID NO 1
<211> LENGTH: 12
<212> TYPE: DNA
<213> ORGANISM: Tobacco rpL34 promoter

<400> SEQUENCE: 1
tataggcccg tc                                                           12

<210> SEQ ID NO 2
<211> LENGTH: 23
<212> TYPE: DNA
<213> ORGANISM: Tobacco rpL34 promoter

<400> SEQUENCE: 2
atgggctaac atgttgatgg gct                                               23

<210> SEQ ID NO 3
<211> LENGTH: 16
<212> TYPE: DNA
<213> ORGANISM: Tobacco rpL34 promoter

<400> SEQUENCE: 3
gtttaaaccc agttta                                                       16

<210> SEQ ID NO 4
<211> LENGTH: 16
<212> TYPE: DNA
<213> ORGANISM: Cauliflower mosaic virus

<400> SEQUENCE: 4
acgtaagcgc ttacgt                                                       16

<210> SEQ ID NO 5
<211> LENGTH: 13
<212> TYPE: DNA
<213> ORGANISM: Artificial Sequence
<220> FEATURE:
<221> NAME/KEY: variation
<222> LOCATION: (13)
<223> OTHER INFORMATION: n is a native or non-native minimal promoter
<223> OTHER INFORMATION: Description of Artificial Sequence: enhancer
      element of the isolated rpL34 promoter

<400> SEQUENCE: 5
tataggcccg tcn                                                          13

<210> SEQ ID NO 6
<211> LENGTH: 25
<212> TYPE: DNA
<213> ORGANISM: Artificial Sequence
<220> FEATURE:
<221> NAME/KEY: variation
<222> LOCATION: (25)
<223> OTHER INFORMATION: n is a native or non-native minimal promoter
```

```
<223> OTHER INFORMATION: Description of Artificial Sequence: enhancer
      element of the isolated rpL34 promoter

<400> SEQUENCE: 6
tataggcccg tctataggcc cgtcn                                           25

<210> SEQ ID NO 7
<211> LENGTH: 61
<212> TYPE: DNA
<213> ORGANISM: Artificial Sequence
<220> FEATURE:
<221> NAME/KEY: variation
<222> LOCATION: (60)
<223> OTHER INFORMATION: n is a native or non-native minimal promoter
<223> OTHER INFORMATION: Description of Artificial Sequence: enhancer
      element of the isolated rpL34 promoter

<400> SEQUENCE: 7
tataggcccg tctataggcc cgtctatagg cccgtctata ggcccgtcta taggcccgtn    60
c                                                                    61

<210> SEQ ID NO 8
<211> LENGTH: 24
<212> TYPE: DNA
<213> ORGANISM: Artificial Sequence
<220> FEATURE:
<221> NAME/KEY: variation
<222> LOCATION: (24)
<223> OTHER INFORMATION: n is a native or non-native minimal promoter
<223> OTHER INFORMATION: Description of Artificial Sequence: enhancer
      element of the isolated rpL34 promoter

<400> SEQUENCE: 8
atgggctaac atgttgatgg gctn                                           24

<210> SEQ ID NO 9
<211> LENGTH: 47
<212> TYPE: DNA
<213> ORGANISM: Artificial Sequence
<220> FEATURE:
<221> NAME/KEY: variation
<222> LOCATION: (47)
<223> OTHER INFORMATION: n is a native or non-native minimal promoter
<223> OTHER INFORMATION: Description of Artificial Sequence: enhancer
      element of the isolated rpL34 promoter

<400> SEQUENCE: 9
atgggctaac atgttgatgg gctatgggct aacatgttga tgggctn                  47

<210> SEQ ID NO 10
<211> LENGTH: 70
<212> TYPE: DNA
<213> ORGANISM: Artificial Sequence
<220> FEATURE:
<221> NAME/KEY: variation
<222> LOCATION: (70)
<223> OTHER INFORMATION: n is a native or non-native minimal promoter
<223> OTHER INFORMATION: Description of Artificial Sequence: enhancer
      element of the isolated rpL34 promoter

<400> SEQUENCE: 10
atgggctaac atgttgatgg gctatgggct aacatgttga tgggctatgg gctaacatgt    60 tgatgggctn                                                           70

<210> SEQ ID NO 11
<211> LENGTH: 65
<212> TYPE: DNA
```

```
<213> ORGANISM: Artificial Sequence
<220> FEATURE:
<221> NAME/KEY: variation
<222> LOCATION: (65)
<223> OTHER INFORMATION: n is a native or non-native minimal promoter
<223> OTHER INFORMATION: Description of Artificial Sequence: enhancer
      element of the isolated rpL34 promoter

<400> SEQUENCE: 11
gtttaaaccc agtttagttt aaacccagtt tagtttaaac ccagtttagt ttaaacccag    60 tttan                                                                65

<210> SEQ ID NO 12
<211> LENGTH: 36
<212> TYPE: DNA
<213> ORGANISM: Artificial Sequence
<220> FEATURE:
<221> NAME/KEY: variation
<222> LOCATION: (36)
<223> OTHER INFORMATION: n is a native or non-native minimal promoter
<223> OTHER INFORMATION: Description of Artificial Sequence: enhancer
      element of the isolated rpL34 promoter

<400> SEQUENCE: 12
tataggcccg tcatgggcta acatgttgat gggctn                              36

<210> SEQ ID NO 13
<211> LENGTH: 71
<212> TYPE: DNA
<213> ORGANISM: Artificial Sequence
<220> FEATURE:
<221> NAME/KEY: variation
<222> LOCATION: (71)
<223> OTHER INFORMATION: n is a native or non-native minimal promoter
<223> OTHER INFORMATION: Description of Artificial Sequence: enhancer
      element of the isolated rpL34 promoter

<400> SEQUENCE: 13
tataggcccg tcatgggcta acatgttgat gggcttatag gcccgtcatg gctaacatg     60 ttgatgggct n                                                         71

<210> SEQ ID NO 14
<211> LENGTH: 106
<212> TYPE: DNA
<213> ORGANISM: Artificial Sequence
<220> FEATURE:
<221> NAME/KEY: variation
<222> LOCATION: (106)
<223> OTHER INFORMATION: n is a native or non-native minimal promoter
<223> OTHER INFORMATION: Description of Artificial Sequence: enhancer
      element of the isolated rpL34 promoter

<400> SEQUENCE: 14
tataggcccg tcatgggcta acatgttgat gggcttatag gcccgtcatg gctaacatg     60 ttgatgggct tataggcccg tcatgggcta acatgttgat gggctn                  106

<210> SEQ ID NO 15
<211> LENGTH: 52
<212> TYPE: DNA
<213> ORGANISM: Artificial Sequence
<220> FEATURE:
<221> NAME/KEY: variation
<222> LOCATION: (52)
<223> OTHER INFORMATION: n is a native or non-native minimal promoter
<223> OTHER INFORMATION: Description of Artificial Sequence: enhancer
      element of the isolated rpL34 promoter

<400> SEQUENCE: 15
```

```
tataggcccg tcatgggcta acatgttgat gggctgttta aacccagttt an          52

<210> SEQ ID NO 16
<211> LENGTH: 103
<212> TYPE: DNA
<213> ORGANISM: Artificial Sequence
<220> FEATURE:
<221> NAME/KEY: variation
<222> LOCATION: (103)
<223> OTHER INFORMATION: n is a native or non-native minimal promoter
<223> OTHER INFORMATION: Description of Artificial Sequence: enhancer
      element of the isolated rpL34 promoter

<400> SEQUENCE: 16
tataggcccg tcatgggcta acatgttgat gggctgttta aacccagttt ataggccc    60 gtcatgggct aacatgttga tgggctgttt aaacccagtt tan                   103

<210> SEQ ID NO 17
<211> LENGTH: 154
<212> TYPE: DNA
<213> ORGANISM: Artificial Sequence
<220> FEATURE:
<221> NAME/KEY: variation
<222> LOCATION: (154)
<223> OTHER INFORMATION: n is a native or non-native minimal promoter
<223> OTHER INFORMATION: Description of Artificial Sequence: enhancer
      element of the isolated rpL34 promoter

<400> SEQUENCE: 17
tataggcccg tcatgggcta acatgttgat gggctgttta aacccagttt ataggccc    60 gtcatgggct aacatgttga tgggctgttt aaacccagtt tatataggcc cgtcatgggc 120
taacatgttg atgggctgtt taaacccagt ttan                             154

<210> SEQ ID NO 18
<211> LENGTH: 20
<212> TYPE: DNA
<213> ORGANISM: Tobacco rpL34 promoter

<400> SEQUENCE: 18
gatgggctta taggcccgtc                                              20

<210> SEQ ID NO 19
<211> LENGTH: 71
<212> TYPE: DNA
<213> ORGANISM: Artificial Sequence
<220> FEATURE:
<223> OTHER INFORMATION: Description of Artificial Sequence: rpL34
      promoter oligonucleotide construct

<400> SEQUENCE: 19
agcttttata ggcccgtctt ataggcccgt cttataggcc cgtcttatag gcccgtctta  60
taggcccgtc a                                                       71

<210> SEQ ID NO 20
<211> LENGTH: 71
<212> TYPE: DNA
<213> ORGANISM: Artificial Sequence
<220> FEATURE:
<223> OTHER INFORMATION: Description of Artificial Sequence: rpL34
      promoter oligonucleotide construct

<400> SEQUENCE: 20
ctagtgacgg gcctataaga cgggcctata agacgggcct ataagacggg cctataagac  60
```

```
gggcctataa a                                                              71

<210> SEQ ID NO 21
<211> LENGTH: 74
<212> TYPE: DNA
<213> ORGANISM: Artificial Sequence
<220> FEATURE:
<223> OTHER INFORMATION: Description of Artificial Sequence: rpL34
      promoter oligonucleotide construct

<400> SEQUENCE: 21
agcttgttta aacccagttt aagtttaaac ccagtttaag tttaacccca gtttaagttt        60
aaacccagtt taaa                                                          74

<210> SEQ ID NO 22
<211> LENGTH: 74
<212> TYPE: DNA
<213> ORGANISM: Artificial Sequence
<220> FEATURE:
<223> OTHER INFORMATION: Description of Artificial Sequence: rpL34
      promoter oligonucleotide construct

<400> SEQUENCE: 22
ctagtttaaa ctgggtttaa acttaaactg ggtttaaact taaactgggt ttaaacttaa        60
actgggttta aaca                                                          74

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: mutated
      sequences in the rpL34 promoter region

<400> SEQUENCE: 23
cggcctgcag ca                                                            12

<210> SEQ ID NO 24
<211> LENGTH: 11
<212> TYPE: DNA
<213> ORGANISM: Artificial Sequence
<220> FEATURE:
<223> OTHER INFORMATION: Description of Artificial Sequence: mutated
      sequences in the rpL34 promoter region

<400> SEQUENCE: 24
ggcctgcagc a                                                             11

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: mutated
      sequences in the rpL34 promoter region

<400> SEQUENCE: 25
cggcctgcag gatcgtcgac cac                                                23

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: mutated
      sequences in the rpL34 promoter region
```

-continued

```
<400> SEQUENCE: 26
ttgtttaaac ccagtttaat gggctaacat gttgatgggg cttataggcc cgtctgattt        60

<210> SEQ ID NO 27
<211> LENGTH: 51
<212> TYPE: DNA
<213> ORGANISM: Tobacco rpL34 promoter

<400> SEQUENCE: 27
gtttaaaccc agtttaatgg gctaacatgt tgatgggctt ataggcccgt c                 51

<210> SEQ ID NO 28
<211> LENGTH: 473
<212> TYPE: DNA
<213> ORGANISM: Tobacco rpL34 promoter

<400> SEQUENCE: 28
agatctctct ttgtattctt attgatgtac tggtttgaag atgaataaaa tctttcattc        60
caccaaaaaa agaatgaaaa taaaatttta atatacatgt tgatatagac aaagaagaaa      120
aaaaaagttg tgattacatt tattgactat ttgatgccaa tatctataac tagagctatt      180
ttctatcaat tatatgggta tgttgttata ccatgccaaa acctcaattc ataatgtgct      240
tgtttaaacc cagtttaatg ggctaacatg ttgatgggct tataggcccg tctgatttcc      300
ttgccagaca ctagtaagta aatgattcta tcatccaata tcaaccgtgg gatctagggc      360
ttgtcccact tatatacact acatatattt aactttcctt tagcccttct gcttcagccc      420
ccaaaacaaa gaaagaagct acagagagaa tagcagcgcc gccgtgaaaa atg            473
```